US011813596B2

(12) United States Patent
Antonietti et al.

(10) Patent No.: US 11,813,596 B2
(45) Date of Patent: Nov. 14, 2023

(54) PHOTOCATALYTIC SYSTEM AND APPLICATIONS THEREOF

(71) Applicant: Max Planck Gesellschaft Zur Förderung Der Wissenschaften E.V, Munich (DE)

(72) Inventors: Markus Antonietti, Nuthetal (DE); Oleksandr Savatieiev, Potsdam (DE); Bogdan Kurpil, Potsdam (DE); Dariya Dontsova, Berlin (DE)

(73) Assignee: MAX PLANCK GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 578 days.

(21) Appl. No.: 16/759,412

(22) PCT Filed: Oct. 27, 2017

(86) PCT No.: PCT/EP2017/077540
§ 371 (c)(1),
(2) Date: Apr. 27, 2020

(87) PCT Pub. No.: WO2019/081036
PCT Pub. Date: May 2, 2019

(65) Prior Publication Data
US 2020/0290029 A1    Sep. 17, 2020

(51) Int. Cl.
*B01J 31/00* (2006.01)
*B01J 31/06* (2006.01)
*B01J 23/06* (2006.01)
*B01J 27/02* (2006.01)
*B01J 31/26* (2006.01)
*B01J 35/00* (2006.01)
(Continued)

(52) U.S. Cl.
CPC ............. *B01J 31/064* (2013.01); *B01J 23/06* (2013.01); *B01J 27/02* (2013.01); *B01J 31/26* (2013.01); *B01J 35/004* (2013.01); *B01J 35/1014* (2013.01); *B01J 35/1019* (2013.01); *C07D 487/16* (2013.01); *B01J 2231/44* (2013.01); *B01J 2231/70* (2013.01); *B01J 2531/002* (2013.01); *B01J 2531/008* (2013.01)

(58) Field of Classification Search
None
See application file for complete search history.

(56) References Cited

U.S. PATENT DOCUMENTS

2017/0240422 A1\*  8/2017  Cooper .................... B01J 6/008

FOREIGN PATENT DOCUMENTS

CN          107051585 A  *  8/2017  ............ B01J 31/183

OTHER PUBLICATIONS

Dontsova et al, Triazoles: A new class of precursors for the synthesis of negatively charged carbon nitride derivatives, chem. mater . . . 27, 15, pp. 5170-5179 (Year: 2015).\*

(Continued)

*Primary Examiner* — Stefanie J Cohen
(74) *Attorney, Agent, or Firm* — CANTOR COLBURN LLP

(57) ABSTRACT

The present invention relates to novel poly(heptazine imides), a photocatalytic system comprising such poly(heptazine imides) and a sulfur source as well as the application thereof in photocatalytic reactions.

17 Claims, 4 Drawing Sheets a)        b)

c)        d)

(51) Int. Cl.
  B01J 35/10    (2006.01)
  C07D 487/16   (2006.01)

(56) References Cited

OTHER PUBLICATIONS

Dontsova et al, supporting information (Year: 2015).*
CN-107051585-A—English translation (Year: 2017).*
Dontsova et al. Triazoies: A New Class of Precursors for the Synthesis of Negatively Charged Carbon Nitride Derivatives, vol. 27, Jul. 14, 2015, pp. 5170-5179.
Dontsova, et al., Supporting Information to "Triazoies A New Class of Precursors for the Synthesis of Negatively Charged Carbon Nitride Derivatives", Chemistry of Materials, vol. 27, Jul. 14, 2015, pp. S1-S21.
Gang et al., Structure and electronic structure of S-doped graphitic C3N4 investigated by density functional theory, Chinese Physics B., vol. 21, No. 10, Oct. 1, 2012, article 107101, 7 pages.
Goettmann, F. et al., "Chemical Synthesis of Mesoporous Carbon Nitrides Using Hard Templates and Their Use as a Metal-Free Catalyst for Friedel-Crafts Reaction of Benzene", Angew. Chem. Int. Ed., 2006, 45, 4467-4471.
International Search Report for International Application No. PCT/EP2017/077540: International Filing Date: Oct. 27, 2017; dated Jul. 24, 2018; 3 pages.
Ishida, T. et al., "Silver-Catalyzed Incorporation of Carbon Dioxide into o-Alkynylaniline Derivatives", Org. Lett., 2013, 15, 848-851.
Savateev A. et al., Towards organic zeolites and inclusion catalysts: heptazine imide salts can exchange metal cations in the solid state, Chemistry—An Asian Journal 2017, 12, 1517-1522.
Savateev et al., "Highly crystalline poly(heptazine imides) by mechanochemical synthesis for photooxidation of various organic substrates using an intriguing electron acceptor-elemental sulfur", Journal of Catalysis, vol. 350, Apr. 28, 2017 pp. 203-211.
Savateev, A et al., Potassium Poly(heptazine imides) from Aminotetrazoles: Shifting Band Gaps of Carbon Nitride-like Materials for More Efficient Solar Hydrogen and Oxygen Evolution ChemCatChem 2017, 9 (1), 167-174.
Wang et al., "Graphene and g-C3N4 Nanosheets Cowrapped Elemental a-Sulfur as a Novel Metal-Free Heterojunction Photocatalyst for Bacterial Inactivation under Visible-Light", Environmental Science and Technology, 2013, 47, p. 8724-8732.
Written Opinion of the International Searching Authority for International Application No. PCT/EP2017/077540; International Filing Date: Oct. 27, 2017; dated Jul. 24, 2018; 8 pages.

* cited by examiner a)  b)

c)  d)

PHOTOCATALYTIC SYSTEM AND APPLICATIONS THEREOF

CROSS-REFERENCE TO RELATED APPLICATIONS

This Application is the U.S. National Stage Application of PCT/EP2017/077540, filed Oct. 27, 2017, which is incorporated by reference in its entirety herein.

FIELD OF THE INVENTION

The present invention relates to novel poly(heptazine imides), a photocatalytic system comprising such poly(heptazine imides) and a sulfur source as well as the application thereof in photocatalytic reactions.

BACKGROUND

In recent years, usage of visible light energy as a driving force for organic synthesis gained significant attention. A large number of articles deals with various special organic dyes or metal complexes, such as Ruthenium and Iridium complexes as photocatalysts.

However, a main drawback of these dyes and complexes is their high price and poor recyclability. Besides, the aforementioned photocatalysts partially decompose during the photoreaction and the organic products are then unavoidably contaminated with organic decomposition products or heavy metals. In order to remove such contaminants energy and material intensive methods such as liquid chromatography are required.

The steadily increasing number of versatile applications of photocatalysis therefore requires enhanced photocatalytic systems with low price, high durability, efficiency and recyclability.

In view thereof carbon nitride based photocatalysts could complement the toolbox of well-acknowledged homogeneous photocatalysts. Carbon nitrides are cheap, thermally and chemically stable, resistant to photobleaching, and environmentally friendly. In addition, carbon nitrides as photocatalysts can expand the spectrum of organic photoreactions and enable reaction conditions under which organic dyes or metal based photocatalysts are not stable at all.

Just recently, the preparation and use of poly(heptazine imides), a sub-class of carbon nitride based photocatalysts was reported in Dontsova, D.; Pronkin, S.; Wehle, M.; Chen, Z.; Fettkenhauer, C.; Clavel, G.; Antonietti, M., "Triazoles: A New Class of Precursors for the Synthesis of Negatively Charged Carbon Nitride Derivatives", Chem. Mater., 2015, 27, 5170-5179. These photocatalysts demonstrated outstanding photocatalytic performance in model water splitting reactions.

Further developments of this type of photocatalysts were disclosed in Savateev, A.; Pronkin, S.; Epping, J. D.; Willinger, M. G.; Wolft C.; Neher, D.; Antonietti, M.; Dontsova, D., Potassium Poly(heptazine imides) from Aminotetrazoles: Shifting Band Gaps of Carbon Nitride-like Materials for More Efficient Solar Hydrogen and Oxygen Evolution. ChemCatChem 2017, 9 (1), 167-174; and in Savateev, A.; Pronkin, S.; Willinger, M.; Antonietti, M.; Dontsova, D., Towards organic zeolites and inclusion catalysts: heptazine imide salts can exchange metal cations in the solid state, Chemistry—An Asian Journal 2017.

Generally, any type of photocatalyst, in particular when involved in photooxidation reactions, requires an electron acceptor to accomplish the desired chemical transformation. Conventional systems typically use molecular oxygen as electron acceptor. However, the formation of hydrogen peroxide as byproduct of the photoreaction gives rise to undesired side-reactions and thus to lower selectivity, corrosion and safety issues, which are critical, especially where reactions shall be performed at commercial scale.

Wang et al., Environmental Science and Technology, 2013, 47, p. 8724-8732 disclose wrapping reduced graphene oxide and graphitic carbon nitride (g-C3N4) sheets on crystals of cyclooctasulfur ($\alpha$-$S_8$). However, this composite material is just used to facilitate oxygen reduction in order to inactivate bacteria but not to catalyse organic synthesis.

As a consequence there was still a need for an effective photocatalytic system allowing high selectivity of photoreactions under smooth conditions.

SUMMARY OF THE INVENTION

According to one aspect of the invention, there is now provided a photocatalytic system comprising
at least one poly(heptazine imide) and
at least one sulfur source.

There are further provided poly(heptazine imides) which are particularly advantageous if used in the aforementioned photocatalytic systems.

In addition, there is provided a process for the photocatalytic oxidiaton or thiolation of organic compounds wherein the oxidation or thiolation is carried out in the presence of the photocatalytic system by irradiation with electromagnetic radiation having a wavelength sufficient to induce the excitation of the at least one poly(heptazine imide).

DETAILED DESCRIPTION OF THE INVENTION

The invention also encompasses all combinations of preferred embodiments, ranges parameters as disclosed hereinafter with either each other or the broadest disclosed range or parameter.

Whenever used herein the terms "including", "for example", "e.g.", "such as" and "like" are meant in the sense of "including but without being limited to" or "for example without limitation", respectively.

Poly(Heptazine Imides)

The photocatalytic system according to the invention comprises at least one poly(heptazine imide) which serves as a photocatalyst when employed in photocatalytic processes.

In one embodiment the term poly(heptazine imide) denotes compounds comprising repeating structural units of formula (I)

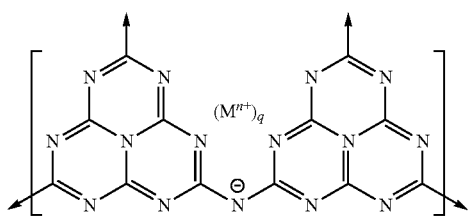

wherein the arrows each denote a bond to a imide group (—NH—) through which two structural units of formula (I) are linked together or a bond to an end group.

$M^{n+}$ denotes an n-valent cation with n being 1, 2 or 3 preferably 1 or 2 and more preferably 1 q is 1/n

In one embodiment the poly(heptazine imides) essentially consist of repeating structural units of formula (I), which in one embodiment means that at least 90 wt.-% of the poly (heptazine imide), preferably 95 wt.-% are repeating units of formula (I) and the imide groups linking them.

In another embodiment the poly(heptazine imides) comprise at least 6 repeating structural units of formula (I).

In one embodiment $M^{n+}$ represents, $H^+$, $Li^+$, $Na^+$, $K^+$, $Rb^+$, $Cs^+$, $Ag^+$, $NH_4^+$, $Zn(OH)^+$, $Mg^{2+}$, $Ca^{2+}$, $Zn^{2+}$, $Co^{2+}$ or $Ni^{2+}$ or mixtures thereof, whereby $Li^+$, $Na^+$, $K^+$, $Zn(OH)^+$, $Mg^{2+}$ and $Ca^{2+}$ or mixtures thereof are preferred and $K^+$ is even more preferred.

Typical end groups of the poly(heptazine imide) include amino groups and cyanamino or —N=C=NH groups, the latter two in particular where 5-aminoetrazole was used as a starting material.

Figure 1:
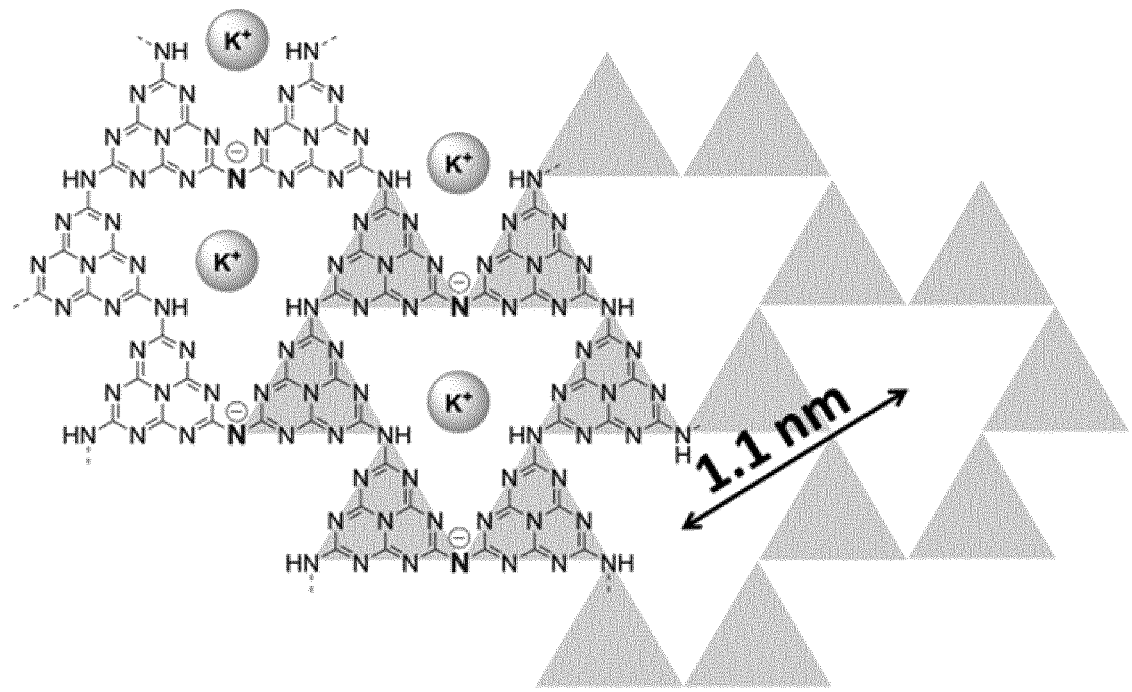
FIG. 1 shows an exemplified and idealized structure of potassium poly(heptazine imide) as identified by X-ray analysis wherein the bis-triangular structures of formula (I) are forming a two-dimensional crystalline network with potassium cations having a distance of around 1.1 nm to each other.

FIG. 1. shows an exemplified and idealized structure of potassium poly(heptazine imide) which was identified by X-ray analysis. It can be seen that the bis-triangular structures of formula (I) are forming a two-dimensional crystalline network wherein the potassium cations have a distance of around 1.1 nm to each other and are surrounded by six heptazine moieties as shown in formula (I) and highlighted in grey in FIG. 1.

Figure 2:
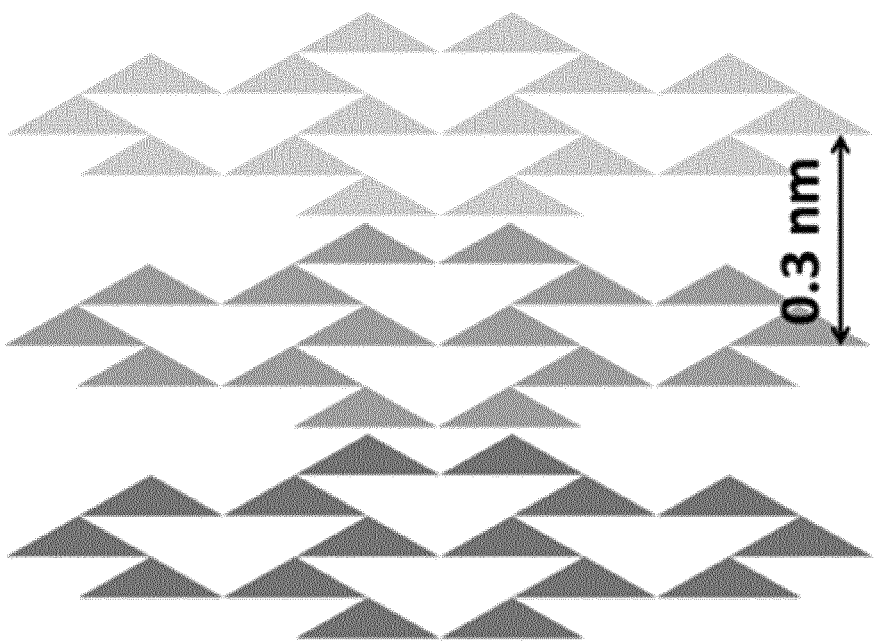
FIG. 2 shows that the two-dimensional crystalline networks of FIG. 1 are arranged in the third dimension by forming a layered structure wherein the layers have a distance of around 0.3 nm with each layer being depicted by different shades of grey.

FIG. 2. further shows how the two-dimensional crystalline networks of FIG. 1 are ideally arranged in the third dimension. As can be seen in this idealized structure potassium poly(heptazine imide) forms a layered structure wherein the layers have a distance of around 0.3 nm with each layer being depicted by different shades of grey. The cations are arranged in channel-like spaces pervading through the three-dimensional structure.

The theoretical emprical formula of the poly(heptazine imides) is $M^{n+}[C_{12}N_{17}H_2^-]_q$ However, it is apparent that the ideal structure can hardly be reached in real life synthesis. Typically, and based on the sum of carbon, nitrogen and hydrogen present in the poly(heptazine imides) the carbon content is between 33.0 and 40.0, preferably between 36.0 and 39.0 wt-%, the nitrogen content is between 56.0 and 63.0 wt-%, preferably between 58.5 and 61.0 wt-% and the hydrogen content between 0.2 and 4.0 wt-%, preferably between 0.5 and 3.0 wt-% whereby the aforementioned contents are selected to add up to 100.0%.

The content of M depends of its mol mass, for potassium poly(heptazine imides) the potassium content is typically 8.5 to 11.5 wt-% preferably 9.5 to 11.0 wt-% based on the sum of carbon, nitrogen and hydrogen present in the potassium poly(heptazine imide).

In another embodiment the potassium content is from 6.0 to 12.0, preferably from 7.0 to 9.5 wt-% based on the total weight of the potassium poly(heptazine imide).

In one embodiment the carbon to nitrogen wt.-ratio (C/N weight ratio) is from 0.55 to 0.70, preferably from 0.60 to 0.66.

It is known to those skilled in art, that due to their insolubility in commonly used media and their preparation process which typically involves a high temperature thermolysis whereby organic precursors are condensed and/or decomposed and/or rearranged, carbon nitrides in general and poly(heptazine imides) in particular may have different properties such as specific surface, band gap, fluorescence lifetime, crystallinity and defects in crystal structure, elemental composition, UV peak adsorption depending on the preparation conditions and precursors.

Further, in particular the end groups may undergo oxidation or hydrolysis when in contact with air and/or humidity. Therefore the poly(heptazine imides) may also have a small content of oxygen e.g. stemming from hydroxyl or carbonyl groups.

Therefore, poly(heptazine imides) may additionally or alternatively also be specified by their preparation process.

In a preferred embodiment potassium poly(heptazine imide) is prepared by a process comprising at least the steps of a) providing a mixture comprising lithium chloride, potassium chloride and 5-aminotetrazole (IUPAC: 1H-Tetrazol-5-ylamine, CAS-No. 4418-61-5 b) heating the mixture provided in step a) to a temperature of 450° C. to 700° C., preferably 500° C. to 700° C., more preferably 500° C. to 650° C. and even more preferably 520 to 620° C. preferably for a duration of at least 60 minutes, preferably at least 2 hours and even more preferably at least 3 hours, for example for 3 to 24 hours or 4 to 12 hours. Longer reaction times are possible but virtually don't add any advantage.

In step a) lithium chloride and potassium chloride are employed. The rationale for this is that the combination of the two salts have a lower melting point than the single components (LiCl: 605° C., KCl: 770° C.). The eutectic mixture of lithium chloride and potassium chloride (44.3 wt-% KCl and 55.7 wt-% LiCl) has a melting point of 357° C. and thus molten mixtures of lithium chloride and potassium chloride were found to be a very good reaction medium to allow the synthesis of poly(heptazine imides) and in particular potassium poly(heptazine imide).

In step a) lithium chloride and potassium chloride are therefore employed for example in a weight ratio of from 0.5:1.0 to 3.0:1.0, preferably of from 0.8:1.0 to 2.0:1.0 and even more preferably of from 1.0:1.0 to 1.5:1.0 such as 1.26:1.00 representing the above mentioned eutectic mixture.

In one embodiment lithium chloride and potassium chloride are molten together first and then used as a preformed mixture e.g. after grinding or milling.

The weight ratio of 5-aminotetrazole to the sum of lithium chloride and potassium chloride is for example 1.0 or less, preferably 0.5 or less such as from 0.05 to 0.50, even more preferably 0.25 or less such as from 0.05 to 0.25.

The mixture comprising lithium chloride, potassium chloride and 5-aminotetrazole may comprise further nitrogen containing organic compounds such as for example melamine, melon and melam. In this case the weight ratio of 5-aminotetrazole to said other nitrogen containing compounds is 2.0 or more, preferably 5.0 or more and even more preferably 10.0 or more.

Typically and most preferably, however, no further nitrogen containing organic compounds are added to the mixture in step a).

In one embodiment lithium chloride, potassium chloride and 5-aminotetrazole are mixed and grinded to allow a good mixing of the solid components.

As a major finding of this invention it was found that a very intense mixing leads to advantageous properties of the resulting potassium poly(heptazine imide). Therefore, in one embodiment step a) includes as a further step milling of the mixture comprising lithium chloride, potassium chloride and 5-aminotetrazole, e.g. using a ball mill, a rod mill a stirred mill or a vibrating mill, whereby a ball mill is preferred.

By milling a number average particle size of 5 to 150 micrometers, preferably from 10 to 100 micrometers and even more preferably 30 to 80 micrometers is obtained.

In contrast thereto manual grinding leads to a number average particle size of 200 to 500 micrometers.

Particle sizes can be measured via dynamic light scattering (DLS).

In one embodiment the heating in step b) to the indicated temperatures is typically performed from ambient temperature to the given temperature or in general from −20° C. to 100° C. to the given temperature.

In one embodiment the heating to the given temperature in step b) is performed at a rate of 0.5 to 40.0° C./min, preferably at a rate of 0.5 to 35.0° C./min.

To avoid oxidative degradation of the products step b) is preferably carried out in an inert atmosphere e.g under nitrogen or argon gas.

The pressure conditions are not specifically limited, and the pressure in step b) may be from 100 hPa to 50 MPa, preferably from 900 hPa to 1 MPa, even more preferred under ambient pressure.

Step b) can further be carried out in any vessel suitable for that purpose. This includes ceramic crucibles, glass or quartz ampoules as long as these vessels are sufficiently stable and inert under the reaction conditions employed.

It was found that potassium poly(heptazine imide) presumably due to the ideal size of the potassium cation is thermodynamically more stable than other poly(heptazine imides).

Nevertheless, poly(heptazine imides) other than potassium poly(heptazine imide) may be prepared by exchanging the potassium cations fully or partially by other cations by simple ion exchange procedures e.g. those disclosed in Savateev, A.; Pronkin, S.; Willinger, M.; Antonietti, M.; Dontsova, D., Towards organic zeolites and inclusion catalysts: heptazine imide salts can exchange metal cations in the solid state, Chemistry—An Asian Journal 2017.

To do this potassium poly(heptazine imide) is for example suspended in a solution of a salt of the desired metal, preferably taken in excess relative to the total potassium content in the solid potassium poly(heptazine imide). Quantitative replacement of ions can be achieved using a dialysis procedure. Typically, the solutions of the metal salts need to have a pH higher than 4 at 25° C. in order to allow substantial replacement of potassium cations.

Where potassium shall be formally replaced by protons, which practically represents the protonation of the deprotonated imide group linking the heptazine moieties as depicted in formula (I), acids can be used. Suitable acids include inorganic or organic acids. Suitable inorganic acids include sulfuric acid and hydrochloric acid.

Large surface areas are typically advantageous in heterogeneous catalysis. It was found that the poly(heptazine imides) according to the invention and prepared starting from 5-aminotetrazoles exhibit a high specific surface, in particular when the starting materials used have particle sizes as described above.

In one embodiment of the invention the poly(heptazine imides) exhibit a BET surface of 10 to 200 $m^2/g$, preferably of 30 to 100 $m^2/g$.

If was found that where the poly(heptazine imides) were prepared from 5-aminotetrazole, lithium and potassium chloride with the small particle sizes as defined above e.g. obtainable by milling, the resulting poly(heptazine imides) exhibit a BET surface of more than 50 to 200 $m^2/g$, preferably of 55 to 100 $m^2/g$, and even more preferably from 70 to 100 $m^2/g$ while the with the larger particle size obtainable e.g. by grinding leads to poly(heptazine imides) having a BET surface of 10 to 50 $m^2/g$, preferably of 30 to 50 $m^2/g$, and even more preferably from 30 to 40 $m^2/g$.

As mentioned above, the crystallinity of the poly(heptazine imides) may have an impact on their electronic properties. In one embodiment of the invention the poly(heptazine imides) exhibit a crystallinity index of 1,000 to 15,000 a.u. (arbitrary units).

If was found that where the poly(heptazine imides) were prepared from 5-aminotetrazole, lithium and potassium chloride with the small particle size as defined above e.g. obtainable by milling, the resulting poly(heptazine imides) exhibit a crystallinity index of for example 10,000 to 15,000 a.u., preferably of 12,000 to 15,000 a.u., while the with the larger particle size obtainable e.g. by grinding the resulting poly(heptazine imides) have a crystallinity index of 1,000 to 4,000 a.u., preferably of 3,000 to 3,800 a.u.

As used herein the "crystallinity index" CI is expressed as $CI=I_{FWHM}/I_{27}$, wherein $I_{FWHM}$ represents the full width at half of the maximum of the largest peak observed in the range of from 26.0 to 28.5° in the powder X-Ray spectrum as measured in accordance with the experimental part and $I_{27}$ represents the height of the highest diffraction peak observed in the same range.

Figure 3:
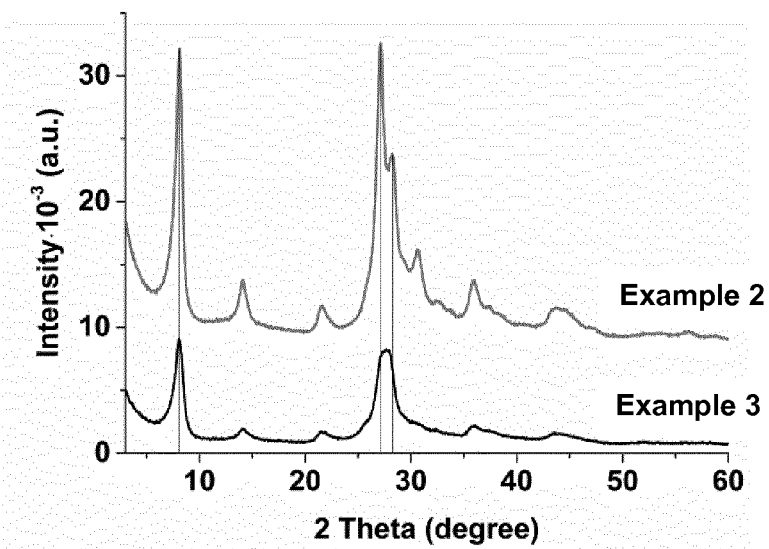
FIG. 3 shows a graph of the "adsorption index" AI which is by $AI=I_G/I_B$, wherein IB represents the maximum of absorbance in the blue region (400-480 nm) and $I_g$ represents the maximum of absorbance in the green region (470-650 nm), each in arbitrary units and as measured by UV-VIS adsorption.
Figure 4:
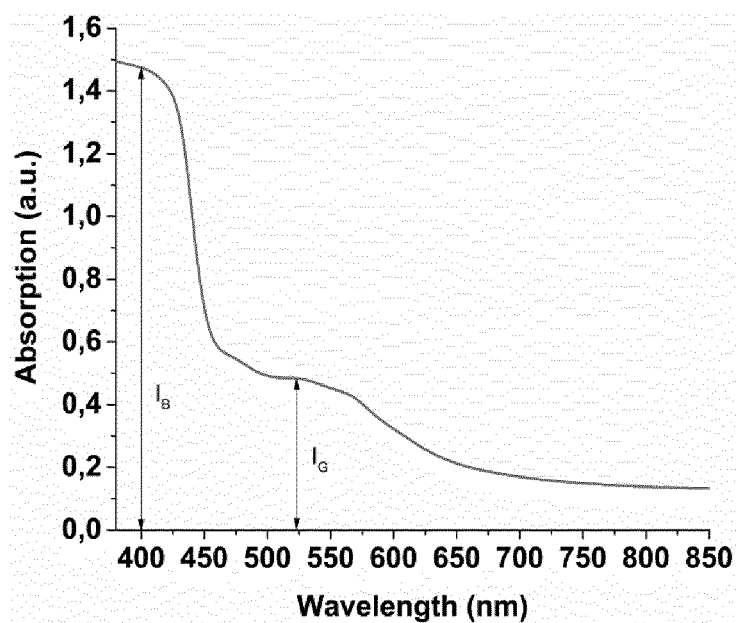
FIG. 4 shows the UV-VIS adsorption spectrum for the poly(heptazine imide) prepared according to example 2 wherein the maximum of absorbance in the blue region (400-480 nm)—$I_b$—and the maximum of absorbance in the green region (470-650 nm)—$I_g$—are indicated, each in arbitrary units.

In one embodiment of the invention the poly(heptazine imides) exhibit an "adsorption index" AI of 0 to 1, preferably 0.1 to 1.0 and even more preferably 0.3 to 0.4 whereby the "absorption index" AI is calculated by $AI=I_G/I_B$, wherein $I_B$ represents the maximum of absorbance in the blue region (400-480 nm) and $I_g$ represents the maximum of absorbance in the green region (470-650 nm), each in arbitrary units, as measured by UV-VIS adsorption. UV-VIS adsorption is measured as described in the experimental part. An illustrative example is given in FIG. 3.

In one embodiment of the invention the poly(heptazine imides) show a fluorescence lifetime of 0.4 to 2 ns, preferably of 0.5 to 2.0 ns and even more preferably from 0.5 to 0.8 ns as measured in accordance with the experimental part.

If was found that where the poly(heptazine imides) were prepared from 5-aminotetrazole, lithium and potassium chloride with the small particle size as defined above e.g. obtainable by milling, the resulting poly(heptazine imides) show a fluorescence lifetime of 0.5 to 2.0 ns, preferably 0.6 to 0.8 ns.

In one embodiment of the invention the poly(heptazine imides) exhibit an optical band gap of 1.70 to 2.90 eV, preferably of 2.10 to 2.80 eV.

If was found that where the poly(heptazine imides) were prepared from 5-aminotetrazole, lithium and potassium chloride with the small particle size as defined above e.g. obtainable after milling, the resulting poly(heptazine imides) exhibit an optical band gap of 2.65 to 2.90 eV, preferably of 2.68 to 2.80 eV, while with the larger particle size obtainable e.g. by grinding leads to poly(heptazine imides) having optical band gap of 2.10 to 2.64 eV, preferably of 2.20 to 2.64 eV. Optical band gaps are measured in accordance with the experimental part.

The poly(heptazine imides) may be used in unsupported form or supported form. Suitable supporting materials may be selected from those commonly used for catalysts and include carbon, alumina, silica and silicates an their known modifications. Preferably, the poly(heptazine imides) are used in unsupported form.

Sulfur Source

The photocatalytic system according to the invention besides at least one poly(heptazine imide) also comprises at least one sulfur source which serves as an electron acceptor when employed in photocatalytic processes. The reduced sulfur species resulting therefrom may further act as a reagent depending on the type of reaction.

Suitable sulfur sources include elemental sulfur in any occurence such as for example $S_8$ in alpha- beta and gamma-modification, polymeric sulfur and all other allotropes currently known, whereby $S_8$ is preferred.

Further suitable sulfur sources include polysulfides such as for example alkaline metal polysulfides of the general formula $M_2S_x$ with M being an alkaline metal such as lithium, sodium or potassium and x being from 2 to 9, preferably 4 to 8.

A most preferred sulfur source is alpha-$S_8$ or simply $S_8$ as most abundant form of elemental sulfur.

Further Components

The photocatalytic system according to the invention may further optionally comprise at least one hydrogen sulfide scavenger i.e. a compound capable of reacting with hydrogen sulfide to form sulfides which are hardly soluble in the reaction medium employed. "Hardly soluble" as defined herein means a solubility of 1.0 g/l or less at ambient temperature. Examples of hydrogen sulfide scavengers include zinc oxide, iron oxides and hydroxides and mixed oxides/hydroxides such as Goethit and other transition metals or hydroxides. In one embodiment a further component of the photocatalytic system is zinc oxide.

Applications

According to one aspect of the invention there is provided a process for the photocatalytic oxidation or photocatalytic thiolation of organic compounds wherein the oxidation or thiolation is carried out in the presence of the photocatalytic system by irradiation with electromagnetic radiation having a wavelength sufficient to excite the at least one poly (heptazine imide).

Therefore, the invention also encompasses the use of the photocatalytic system according to the invention in photocatalytic reactions in particular in photocatalytic oxidations and photocatalytic thiolations.

As used herein the oxidation of organic compounds includes all reactions wherein the formal oxidation state of at least one carbon atom is increased.

As used herein thiolation of organic compounds includes all reactions wherein at least one C—H bond is converted into a C—S bond or two geminal C—H bonds are converted into a C=S bond.

The aforementioned thiolation reactions include the following reaction types.

A) Thiolation of benzylic C—H bonds to obtain diaryldisulfanes or poly(aryldisulfanes)

B) Thiolation of amines to thioamides

The aforementioned oxidation reactions include the following rection types.

C) Oxidation of alcohols to aldehydes or ketones

D) Oxidative conversion of dihydropyridines to pyridines

E) Oxidative conversion of N-carboxylated hydrazones to oxadiazoles

More specifically the aforementioned thiolation and oxidation reactions and thus the invention encompasses the following processes:

A i): A process for the preparation of a compound of formula (IIc)

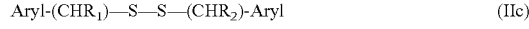

Aryl-(CHR$_1$)—S—S—(CHR$_2$)-Aryl  (IIc)

wherein $R_1$ and $R_2$ are either different or identical and represent hydrogen or alkyl and Aryl represents aryl or heteroaryl comprising irradiating a reaction mixture comprising a compound of formula (IIa)

Aryl-(CH$_2$R$_1$)  (IIa)

wherein $R_1$ has the meaning set forth above
and if $R_2$ differs from $R_1$ additionally
a compound of formula (IIb)

Aryl-(CH$_2$R$_2$)  (IIb)

wherein $R_2$ has the meaning set forth above
and
a photocatalytic system according to the invention.

A ii): A process for the preparation of a compound comprising a plurality of at least one of the structural units of formula (IIIc)

Aryl(CH$_2$R$_3$)$_m$[(CHR$_3$)—S]$_n$—  (IIIc)

wherein n+m is an integer of 2, 3, 4, 5 or 6 the n residues $R_3$ are either different or identical and represent hydrogen or alkyl and Aryl represents aryl oder heteroaryl which is substituted m-fold by residues (CH$_2$R$_3$) and n-fold by residues [(CHR$_3$)—S]— whereby the structural units of formula (IIIc) are bound together via a S—S bond formed by two [(CHR$_3$)—S]— residues of two structural units of formula (IIIc)

comprising irradiating a reaction mixture comprising
at least one compound of formula (IIIa)

$$Aryl(CH_2R_3)_{m+n} \quad (IIIa)$$

wherein $R_3$ has the meaning set forth above
and
a photocatalytic system according to the invention.

B i) A process for the preparation of a compound of formula (IVb)

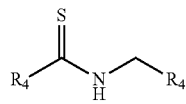
(IVb)

wherein
the two $R_4$ independently of each other, preferably identically represent hydrogen, alkyl, aryl, heterocyclyl, alkenyl or alkynyl
comprising irradiating a reaction mixture comprising
at least one, preferably one compound of formula (IVa)

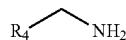
(IVa)

wherein $R_4$ has the meaning set forth above
and
a photocatalytic system according to the invention.

B ii)
A process for the preparation of a compound of formula (Vc)

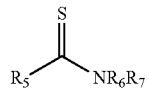
(IVc)

wherein
$R_5$ represents hydrogen, alkyl, aryl, heterocyclyl, alkenyl or alkynyl and
$R_6$ and $R_7$ independently of each other, preferably identically represent alkyl, aryl, heterocyclyl, alkenyl or alkynyl or
$R_6$ and $R_7$ together represent alkanediyl or alkenediyl
comprising irradiating a reaction mixture comprising
at least one, preferably one compound of formula (Va)

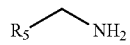
(Va)

wherein $R_5$ has the meaning set forth above
at least one, preferably one compound of formula (Vb)

$$HNR_6R_7 \quad (Vb)$$

wherein $R_6$ and $R_7$ have the meaning set forth above
and
a photocatalytic system according to the invention.

B iii) A process for the preparation of compounds of formula (VIb)

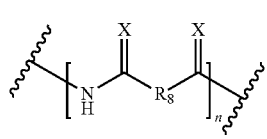
(VIb)

wherein
n represents an integer of 2 or more, preferably from 2 to 6
$R_8$ represents alkanediyl, aryldiyl or alkenediyl
X represents either one sulfur atom or two hydrogen atoms bound to the carbon under the proviso that at maximum one C=S group is adjacent to each nitrogen atom and
wherein the end groups of the compounds of formula (VIb) are hydrogen atoms
comprising irradiating a reaction mixture comprising
at least one, preferably one compound of formula (VIa)

$$H_2N\diagup R_8 \diagdown NH_2 \quad (Va)$$

wherein $R_8$ has the meaning set forth above
and
a photocatalytic system according to the invention.

C) A process for the preparation of a compound of formula (VIIb)

$$\underset{R_9 \quad R_{10}}{\overset{O}{\|}} \quad (VIIb)$$

wherein
$R_9$ and $R_{10}$ independently of each other represent hydrogen, alkyl, aryl, heterocyclyl, alkenyl or alkynyl or
$R_9$ and $R_{10}$ together represent alkanediyl or alkenediyl
comprising irradiating a reaction mixture comprising
a compound of formula (VIIa)

$$\underset{R_9 \quad R_{10}}{\overset{HO \quad OH}{\diagdown \diagup}} \quad (VIIa)$$

wherein $R_9$ and $R_{10}$ have the meaning set forth above
and
a photocatalytic system according to the invention.

D i). A process for the preparation of a compound of formula (VIIIc)

(VIIIc)

wherein

R$_{11}$ and R$_{13}$ independently of each other represent hydrogen, alkyl, aryl, heterocyclyl, alkenyl or alkynyl R$_{12}$ and represents hydrogen, alkyl, aryl, heterocyclyl, alkenyl or alkynyl comprising irradiating a reaction mixture comprising a compound of formula (VIIIa)

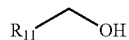

(VIIIa)

wherein R$_{11}$ has the meaning set forth above and at least one, preferably one compound of formula (VIIIb)

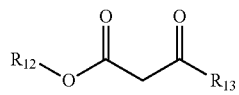

(VIIIb)

and ammonia or a ammonium-salt, preferably an ammonium salt which is preferably ammonium hydrogencarbonate and a photocatalytic system according to the invention.

D ii) A process for the preparation of a compound of formula (IXb)

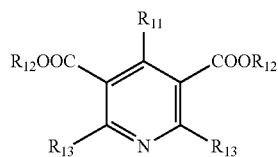

(IXb)

wherein

R$_{11}$, R$_{12}$ and R$_{13}$ have the same meaning as given for formula (VIIIc) above including their areas of preference comprising irradiating a reaction mixture comprising a compound of formula (VIIIc)

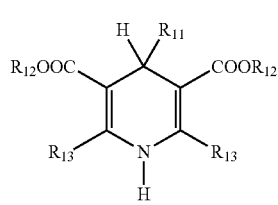

(VIIIc)

and a photocatalytic system according to the invention.

E) A process for the preparation of a compound of formula (Xb)

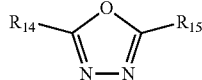

(Xb)

wherein

R$_{14}$ and R$_{15}$ independently of each other represent hydrogen, alkyl, aryl, heterocyclyl, alkenyl or alkynyl or comprising irradiating a reaction mixture comprising a compound of formula (Xa)

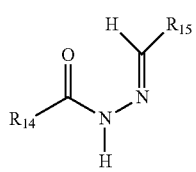

(Xa)

wherein R$_{14}$ and R$_{15}$ have the meaning set forth above and a photocatalytic system according to the invention.

As used herein for all processes listed above the alkyl, alkenyl, alkynyl, alkanediyl and alkenediyl substituents as defined above are either not, once, twice or more than twice interrupted by non-successive functional groups selected from the group consisting of:

—O—, —S—, —SO$_2$—, —SO—, —SO$_2$NR$^{16}$—, NR$^{16}$SO$_2$—, —NR$^{16}$—, —CO—, —O(CO)—, (CO)O—, —O(CO)O—, —NR$^{16}$(CO)NR$^{16}$—, NR$^{16}$(CO)—, —(CO)NR$^{16}$—, —NR$^{16}$(CO)O—, —O(CO)NR$^{16}$—, —Si(R$^{17}$)$_2$—, —OSi(R$^{17}$)$_2$—, —OSi(R$^{17}$)$_2$O—, —Si(R$^{17}$)$_2$O—, and either not, once, twice or more than twice interrupted by bivalent residues selected from the group consisting of heterocyclo-diyl, and aryldiyl, and either not, once, twice or more than twice substituted by substituents selected from the group consisting of:

oxo, hydroxy, halogen, nitro, cyano, C$_6$-C$_{14}$-aryl, C$_1$-C$_8$-alkoxy, C$_1$-C$_8$-alkylthio, —SO$_3$H, —SO$_3$M, —COOH, —PO$_3$H$_2$, —PO$_3$HM, —COOM, PO$_3$M$_2$, —PO(N(R$^{17}$)$_2$)$_2$, PO(OR$^{17}$)$_2$, —SO$_2$N(R$^{16}$)$_2$, —N(R$^{16}$)$_2$, —CO$_2$N(R$^{17}$)$_2$, —COR$^{16}$, —OCOR$^{16}$, —NR$^{16}$(CO)R$^{17}$, —(CO)OR$^{16}$, —NR$^{16}$(CO)N(R$^{16}$)$_2$, —Si(OR$^{17}$)$_y$(R$^{17}$)$_{3-y}$, —OSi(OR$^{17}$)$_y$(R$^{17}$)$_{3-y}$, with y=1, 2 or 3 whereby in all above formulae where used

R$^{16}$ is independently selected from the group consisting of hydrogen, C$_1$-C$_8$-alkyl, C$_6$-C$_{14}$-aryl, and heterocyclyl or N(R$^{16}$)$_2$ as a whole is a N-containing heterocycle, R$^{17}$ is independently selected from the group consisting of C$_1$-C$_8$-alkyl, C$_6$-C$_{14}$-aryl, and heterocyclyl or N(R$^{17}$)$_2$ as a whole is a N-containing heterocycle M is hydrogen, or 1/q equivalent of an q-valent metal ion or is an ammonium ion or a guanidinium ion or a primary, secondary, tertiary or quarternary organic ammonium ion, in particular those of formula [N(C$_1$-C$_{18}$-alkyl)$_s$H$_t$]$^+$ wherein s is 1, 2 or 3 and t is (4-s).

In one specific embodiment the alkyl, alkenyl, alkynyl, alkanediyl and alkenediyl substituents as defined above are
either not or once interrupted by non-successive functional groups selected from the group consisting of: —O—, —CO—, —O(CO)—, (CO)O—, —NR$^{16}$(CO)—, —(CO)NR$^{16}$—,
and
either not, once, twice or more than twice substituted by substituents selected from the group consisting of: halogen, cyano, $C_6$-$C_{14}$-aryl In another specific embodiment the alkyl, alkenyl, alkynyl, alkanediyl and alkenediyl substituents as defined above are neither interrupted by functional groups nor substituted by any substituents selected from the group consisting of:

As used herein for all processes listed above aryl denotes carbocyclic aromatic substituents preferably having six to fifteen carbon atoms within the aromatic system as such, i.e. without carbon atoms of optional substituents and are preferably phenyl ($C_6$), naphthyl ($C_{10}$), phenanthrenyl and anthracenyl (each $C_{14}$), whereby said carbocyclic, aromatic substituents are unsubstituted or substituted by up to five identical or different substituents per cycle. For example and with preference, the substituents are selected from the group consisting of fluoro, bromo, chloro, iodo, nitro, cyano, formyl or protected formyl, hydroxyl or protected hydroxyl, $C_1$-$C_8$-alkyl, $C_1$-$C_8$-haloalkyl, $C_1$-$C_8$-alkoxy, $C_1$-$C_8$-haloalkoxy, $C_6$-$C_{14}$-aryl, in particular phenyl and naphthyl, di($C_1$-$C_8$-alkyl)amino, ($C_1$-$C_8$-alkyl)amino, CO($C_1$-$C_8$-alkyl), OCO($C_1$-$C_8$-alkyl), NHCO($C_1$-$C_8$-alkyl), N($C_1$-$C_8$-alkyl)CO($C_1$-$C_8$-alkyl), CO($C_6$-$C_{14}$-aryl), OCO($C_6$-$C_{14}$-aryl), NHCO($C_6$-$C_{14}$-aryl), N($C_1$-$C_8$-alkyl)CO($C_6$-$C_{14}$-aryl), COO—($C_1$-$C_8$-alkyl), COO—($C_6$-$C_{14}$-aryl), CON($C_1$-$C_8$-alkyl)$_2$ or CONH($C_1$-$C_8$-alkyl), $CO_2M$, $CONH_2$, $SO_2NH_2$, $SO_2N(C_1$-$C_8$-alkyl)$_2$, $SO_3M$ and $PO_3M_2$.

In another embodiment, the carbocyclic, aromatic substituents are unsubstituted or substituted by up to three identical or different substituents per cycle selected from the group consisting of fluoro, chloro, cyano, $C_1$-$C_8$-alkyl, $C_1$-$C_8$-haloalkyl, $C_1$-$C_8$-alkoxy, $C_1$-$C_8$-haloalkoxy, $C_6$-$C_{14}$-aryl, in particular phenyl.

In another embodiment the carbocyclic, aromatic substituents are unsubstituted or substituted by up to three identical or different substituents per cycle selected from the group consisting of fluorine, $C_1$-$C_8$-alkyl, $C_1$-$C_8$-perfluoroalkyl, $C_1$-$C_8$-alkoxy, $C_1$-$C_8$-perfluoroalkoxy, and phenyl.

In another embodiment aryl denotes phenyl.

The definitions given above including their areas of preference also apply analogously to aryldiyl substituents.

As used herein and unless specifically stated otherwise heterocyclyl denotes heterocyclic aliphatic, aromatic or mixed aliphatic and aromatic substituents in which no, one, two, three or four skeleton atoms per cycle, but at least one skeleton atom in the entire cyclic system is a heteroatom selected from the group consisting of nitrogen, sulphur and oxygen and whereby the entire cyclic system as such, i.e. without carbon atoms of substituents, comprises one to fifteen carbon atoms and whereby the heterocyclic aliphatic, aromatic or mixed aliphatic and aromatic substituents are unsubstituted or substituted if possible by up to five identical or different substituents per cycle, whereby the substituents are selected from the same group as given above for carbocyclic aromatic substituents including the areas of preference. Aromatic heterocyclyl is also referred to as heteroaryl.

In one embodiment heterocyclyl denotes pyridinyl, oxazolyl, thiophen-yl, benzofuranyl, benzothiophen-yl, dibenzofuranyl, dibenzothiophenyl, furanyl, indolyl, pyridazinyl, pyrazinyl, imidazolyl, pyrimidinyl and quinolinyl, either unsubstituted or substituted with up to three substituents selected from the group consisting of fluorine, $C_1$-$C_8$-alkyl, $C_1$-$C_8$-perfluoroalkyl, $C_1$-$C_8$-alkoxy, $C_1$-$C_8$-perfluoroalkoxy, and phenyl.

As used herein, and unless specifically stated otherwise, protected formyl is a formyl substituent which is protected by conversion to an aminal, acetal or a mixed aminal acetal, whereby the aminals, acetals and mixed aminal acetals are either acyclic or cyclic.

For example, and with preference, protected formyl is 1,1-(2,4-dioxycyclopentanediyl).

As used herein, and unless specifically stated otherwise, protected hydroxyl is a hydroxyl radical which is protected by conversion to a ketal, acetal or a mixed aminal acetal, whereby the aminals, acetals and mixed aminal acetals are either acyclic or cyclic. A specific example of protected hydroxyl is tetrahydropyranyl (O-THP).

As used herein, and unless specifically stated otherwise, alkyl, alkanediyl, alkoxy, alkylthio, alkenyl, alkynyl, alkenediyl and alkinediyl denote and include straight-chain, cyclic either in part or as a whole, branched or unbranched alkyl, alkanediyl, alkoxy, alkylthio, alkenyl, alkenediyl and alkinediyl substituents having, where indicated, the given number of carbon atoms in the substituent as such, i.e. without carbon atoms of further, optionally present substituents or carbon atoms or functions interrupting the aforementioned substituents. As an example, a benzyl substituent represents a $C_1$-alkyl substituted by phenyl.

Preferred alkyl, alkanediyl, alkoxy, alkylthio, alkenyl, alkynyl, alkenediyl and alkinediyl denotes $C_1$-$C_{12}$-alkyl, $C_1$-$C_{12}$-alkanediyl, $C_1$-$C_{12}$-alkoxy, $C_1$-$C_{12}$-alkylthio, $C_2$-$C_{12}$-alkenyl, $C_2$-$C_{12}$-alkenediyl and $C_2$-$C_{12}$-alkynediyl.

Haloalkyl or haloalkoxy substituents denote alkyl or alkoxy substituents with the given number of carbon atoms which are once or more than once, preferably fully substituted by halogen.

Fluoroalkyl or fluoroalkoxy substituents denote alkyl or alkoxy substituents with the given number of carbon atoms which are once or more than once, preferably fully substituted by fluorine.

Perfluoroalkyl or perfluoroalkoxy substituents denote alkyl or alkoxy substituents with the given number of carbon atoms which are fully substituted by fluorine.

Specific examples of alkyl are methyl, ethyl, n-propyl, isopropyl, n-butyl, tert-butyl, n-pentyl, cyclohexyl, n-hexyl, n-heptyl, n-octyl and isooctyl. Additional examples for $C_1$-$C_{18}$-alkyl are norbornyl, adamantyl, n-decyl, n-dodecyl alkyl, n-hexadecyl, n-octadecyl.

Specific examples of alkanediyl are methylene, 1,1-ethylene, 1,2-ethylene, 1,1-propylene, 1,2-propylene, 1,3-propylene, 1,1-butylene, 1,2-butylene, 2,3-butylene, 1,4-butylene, 1,5-pentylene, 1,6-hexylene, 1,1-cyclohexylene, 1,4-cyclohexylene, 1,2-cyclohexylene and 1,8-octylene.

Specific examples of alkoxy-substituents are methoxy, ethoxy, isopropoxy, n-propoxy, n-butoxy, tert-butoxy and cyclohexyloxy.

Specific examples of alkenyl-substituents are allyl, 3-propenyl and buten-2-yl.

Specific examples of alkynyl-substituents are ethinyl and 1,3-propinyl.

Reaction Conditions

The processes according to the invention described above comprise irradiating a reaction mixture comprising a photocatalytic according to the invention.

With the poly(heptazine imides) used herein excitation is typically induced by irradiation with electromagnetic radiation having a wavelength of 200 to 700 nm, preferably from 350 to 650 nm, more preferably in the range of 350 to 550 nm, even more preferably in the range of 450 to 500 nm such as for example 460 to 500 nm.

Suitable sources of electromagnetic radiation having a wavelength sufficient to induce the generation of radicals include eximer lasers such as Argon fluoride-lasers; UV lamps like low-pressure, medium-pressure, high-pressure and super-high-pressure mercury lamps which can be undoped or doped e.g. with gallium iodide, thallium iodide or other metal halides; green, blue, violet or violet-blue LEDs; unconcentrated or concentrated, direct or indirect sunlight; microwave-excited metal vapour lamps; excimer lamps, fluorescent lamps; and noble gas incandescent lamps.

Preferred sources are blue, violet or violet-blue LEDs, preferably those with a maximum emission at 461 nm; unconcentrated or concentrated, direct or indirect sunlight.

In an embodiment, multichromatic sources of electromagnetic radiation are used to generate radicals.

As used herein a multichromatic sources of electromagnetic radiation denotes a source emitting electromagnetic radiation having more than one relative emission maxima (also known as emission bands) preferably more than one relative emission maxima within the wavelength ranges disclosed above.

It is apparent to those skilled in the art that excitation and thus the reaction depends on the intensity and/or the time of irradiance.

The reaction may for example be from 5 s to two weeks, preferably from one minute to 168 hours, more preferably and typically from 30 minutes to 72 hours.

The amount of poly(heptazine imides) employed in the photocatalytic reactions is not critical at all a may for example be from 0.1 wt-% to 1.000 wt-%, preferably from 1 wt-% to 100 wt-% based on the organic compound to be oxidized or thiolated.

The amount of the sulfur source, in particular elemental sulfur employed in the photocatalytic reactions may for example be from 20 mol-% to 10.000 mol-% calculated on sulfur atoms and based on the organic substrate to be oxidized or thiolated, preferably from 50 to 1.000 mol-%. Higher amounts are possible but add no advantage.

Where thiolations are performed a preferred amount of sulfur source, in particular elemental sulfur employed in the photocatalytic reactions may for example be from 40 mol-% to 10.000 mol % calculated on sulfur atoms and based on the organic substrate to be thiolated, preferably from 75 to 1.000 mol-%.

The determination of a suitable reaction temperature range during the processes according to the invention inter alia depends on the organic compound to be oxidized or thiolated, the solvent and the reaction type. However, as a general guideline the oxidation reactions are typically carried out at a temperature of from −20° C. to 100° C., preferably from 15 to 100° C. and even more preferably from 25 to 75° C. such as for example 50 to 80° C.

The reaction pressure may vary from 100 hPa to 10 MPa, preferably from 900 hPa to 1 MPa and more preferably from 900 hPa to 0.2 MPa, e.g. under ambient pressure.

Providing the reaction mixures comprising the compounds set forth above may occur in any manner known to those skilled in the art, in any order of addition and in any vessel known to skilled in the art to allow irradiation as defined above.

The processes according to the invention may be carried out either with or, in particular where the organic compounds employed in the reation are liquid at the desired reaction temperature, without a solvent.

Suitable solvents are those which do not or virtually not react under reaction conditions. Such solvents include aromatic hydrocarbons such as benzene, toluene and the isomeric xylenes; ethers such as diethylether, methyl tert.-butyl ether, tetrahydrofurane, dioxane, dimethoxyethane, diethoxyethan and higher glycolethers; amides such as dimethylformamide; sulfones such as tetraethylensulfone; esters such as ethylacetate; halogenated hydrocarbons such as chlorobenzene, dichloromethane and tetrachloroethane, nitriles such as acetonitrile and benzonitrile and mixtures of the aforementioned solvents.

It was found that in many case halogenated hydrocarbons such as dichloromethane, or nitriles such as acetonitrile and benzonitrile are the solvents of choice.

A major advantage of the present invention is the possibility to perform a large variety of synthetic processes involving a thiolation or oxidation highly selective with high conversion and under smooth conditions using the inventive photocatalytic system comprising poly(heptazine imides) as a sulfur source as an electron acceptor and the latter optionally also as a reagent. The poly(heptazine imides) can be recycled numerous times without loss of activity.

In the following, the present invention is illustrated by examples which however not intended to limit the scope of invention.

Experimental Section

General Information

Materials. Lithium chloride (≥99%) was purchased from Carl Roth; 5-aminotetrazole was purchased from Santa Cruz biotechnology; potassium chloride (≥99.5) was purchased from Sigma Aldrich. All the chemicals were used without further purification.

Acetonitrile-$d_3$ (≥99.8 atom % D), chloroform-d (99.8 atom % D), toluene (99.8%), 4-methylanisole (99%), 2-methylanisole (99%), p-tolunitrile (98%), ethylbenzene (99.8%), p-iodotoluene (99%), sulfur (≥99.5%), $TiO_2$ used for comparative examples (99.5%, a mixture of rutile and anatase) were purchased from Sigma-Aldrich. 1,2-dibenzyldisulfane (98+%), benzylthiol (99%) were purchased from Alfa Aesar. Acetonitrile (hypergrade for LC-MS) and N,N,4-trimethylaniline (for synthesis) were purchased from Merck. P-fluorotoluene (97%) and dibenzylsulfide (98%) were purchased from Acros Organics.

tert-butyl p-tolylcarbamate was prepared according to Ishida, T.; Kikuchi, S.; Tsubo, T.; Yamada, T., "Silver-Catalyzed Incorporation of Carbon Dioxide into o-Alkynylaniline Derivatives", Org. Lett., 2015, 15, 848-851. Mesoporous graphitic carbon nitride (mpg-CN) used for comparative examples was prepared according to Goettmann, F.; Fischer, A.; Antonietti, M.; Thomas, A., "Chemical Synthesis of Mesoporous Carbon Nitrides Using Hard Templates and Their Use as a Metal-Free Catalyst for Friedel-Crafts Reaction of Benzene", Angew. Chem., Int. Ed., 2006, 45, 4467-4471.

Characterization $^1H$ and $^{13}C$ NMR spectra were recorded on Varian or Agilent 400 MHz (at 400 MHz for Protons and 101 MHz for Carbon-13). Chemical shifts are reported in ppm downfield from TMS ($^1H$, $^{13}C$) as an internal standard.

High-resolution mass spectral data were obtained using Waters XEVO G2-XS QTOF with Aquity H-Class (HPLC).

Powder X-Ray diffraction patterns were measured on a Bruker D8 Advance diffractometer equipped with a scintillation counter detector with CuKα radiation (λ=0.15418 nm) applying 2θ step size of 0.05° and counting time of 3 s per step.

Nitrogen adsorption/desorption measurements to calculate the BET surface were performed after degassing the samples at 150° C. for 20 hours using a Quantachrome Quadrasorb SI-MP porosimeter at 77.4 K. The specific surface areas were calculated by applying the Brunauer-Emmett-Teller (BET) model to adsorption isotherms for 0.05<p/p0<0.3 using the QuadraWin 5.05 software package.

Elemental analysis (EA) was accomplished as combustion analysis using a Vario Micro device. Scanning electron microscopy (SEM) images were obtained on a LEO 1550-Gemini microscope.

Transmission electron microscopy (TEM) was performed on a CM200FEG (Philips) microscope, operated at 200 kV. Samples were prepared by depositing a drop of a suspension of particles in ethanol onto the amorphous carbon film.

Optical absorbance spectra of powders were measured on a Shimadzu UV 2600 equipped with an integrating sphere. The emission spectra were recorded on LS-50B, Perkin Elmer instrument. The excitation wavelength was 350 nm. EDS investigations were conducted on a Link ISIS-300 system (Oxford Microanalysis Group) equipped with a Si(Li) detector and an energy resolution of 133 eV.

Time-resolved fluorescence measurements were performed by using a single photon counting setup (TCSPC) with a Becker&Hickl PML-spectrometer (modified Oriel MS-125) with a laser repetition rate of 2 MHz. The detector comprises a Becker&Hickl PML-16-C-1 (modified Hamamatsu) multi-alkaline photomultiplier. The excitation wavelength was 405 nm. The excitation was carried out using a pulsed laser diode at ~30 nJ/cm$^2$ (LDH-P-C405, PicoQuant GmbH). The emission was recorded in the range of 460-600 nm, while blocking the secondary detection of the excitation pulses with a 450 nm cut-off-filter. Raw decay data presented as logarithm of photon counts versus time were analyzed with data analysis software of PicoQuant GmbH (Germany). The decay times were extracted by means of a reconvolution fit based on a double and triple exponential model.

Considering that $$I_{PL}(t) = \sum_{i=1}^{i=n} a_i e^{-t/\tau_i}$$

where $\tau_i$ is the lifetime and $a_i$ is the amplitude of the $i^{th}$ component, the intensity-averaged fluorescence lifetime τ was calculated as $$\langle \tau \rangle = \sum_{i=1}^{i=n} a_i \tau_i^2 \bigg/ \sum_{i=1}^{i=n} a_i \tau_i$$

Milling was carried out with ball mill Retsch MM400, ball milling cup Retsch 1.4112 (50 mL) and a steel ball (diameter 25 mm, weight 63 g).

Irradiance of the LED modules was measured using PM400 Optical Power and Energy Meter equipped with integrating sphere S142C that were purchased from THORLABS.

Examples 1 to 3: Preparation of Poly(Heptazine Imides)

Example 1: Preparation of LiCl/KCl Eutectics

A steel ball mill cup (ca. 25 mL) was charged with LiCl (2.25 g) and KCl (2.75 g). The steel ball was placed into the cup and mixture was homogenized using ball mill (20 s$^{-1}$, 2 min). The powder was transferred into a porcelain crucible, covered with a lid and placed into the oven. The temperature inside the oven was increased from 20° C. to 580° C. within 4 hours under flow of nitrogen, hold at 580° C. for 4 h and allowed to cool to room temperature. The solid was removed from the crucible and crushed into a fine powder using ball mill. The prepared eutectics is hygroscopic solid that should be used right after preparation. Yield: 4.97 g, 99%.

Example 2: Preparation of Potassium Poly(Heptazine Imide) with Additional Milling of Precursors A mixture of 5-aminotetrazole (0.99 g) and LiCl/KCl eutectics (4.97 g) prepared according to example 1 was brought together into a steel ball mill cup. The steel ball was placed and the cup was closed. The mixture of precursors has been grinded for 5 min at the shaking rate 25 s$^{-1}$ resulting in a number average particle size of around 75 micrometers. Resultant flour-like white powder was transferred into a porcelain crucible, covered with a porcelain lid and placed into the oven. The temperature inside the oven was increased from 20° C. to 600° C. within 4 hours under flow of nitrogen (15 L·min$^{-1}$) after which it was maintained at 600° C. for another 4 hours. After that the oven was allowed to cool to room temperature. The melt from the crucible was transferred into a beaker, deionized water (50 mL) and stir bar were added into a beaker. The suspension was kept at stirring at room temperature for 4 hours until suspension became highly homogeneous and no agglomerated particles were seen. The solid was separated by centrifugation (6500 min$^{-1}$, 12 min), washed with water (3×2 mL) using centrifuge to separate particles of the material (13500 min$^{-1}$, 1 min) and dried in vacuum giving 256 mg of potassium poly(heptazine imide) as a dark-yellow material.

BET-Surface: 89 m$^2$/g
Optical bandgap: 2.73 eV
Elemental composition (in wt-%): C: 34.2; N: 51.6; H: 2.3; O: 3.8; K: 7.8; Cl: 0.4
C/N ratio: 0.663
Fluorescence time: 0.62 ns
Adsorption index: 0.327 a.u.
Cristallinity Index: 12,316 a.u.

Example 3: Preparation of Potassium Poly(Heptazine Imide) with Manual Grinding of Precursors A mixture of 5-aminotetrazole (0.99 g) and LiCl/KCl eutectics (4.97 g) prepared according to example 1 has been grinded manually in a mortar for 10 min resulting in a number average particle size of around 300 micrometer. Resultant white powder was transferred into a porcelain crucible, covered with a porcelain lid and placed into the oven. The temperature inside the oven was increased from 20° C. to 600° C. within 4 hours under flow of nitrogen (15 L·min$^{-1}$) after which it was maintained at 600° C. for another 4 hours. After that the oven was allowed to cool to room temperature. The melt from the crucible was transferred into a beaker, deionized water (50 mL) and stir bar were added into a beaker. The suspension was kept at stirring at room temperature for 4 hours until suspension became highly homogeneous and no agglomerated particles were seen. The solid was separated by centrifugation (6500 min$^{-1}$, 12 min), washed with water (3×2 mL) using centrifuge to separate particles of the material (13500 min$^{-1}$, 1 min) and dried in vacuum giving 267 mg of potassium poly(heptazine imide) as a dark-yellow material.

BET-Surface: 40 m$^2$/g
Optical bandgap: 2.62 eV
Elemental composition (in wt-%): C: 32.7; N: 52.6; H: 2.4; O: 2.6; K: 9.7, Cl: 0.0
C/N ratio: 0.621
Fluorescence time: 0.48 ns
Adsorption index: 0.594 a.u.
Cristallinity Index: 3,788 a.u.

Figure 5:
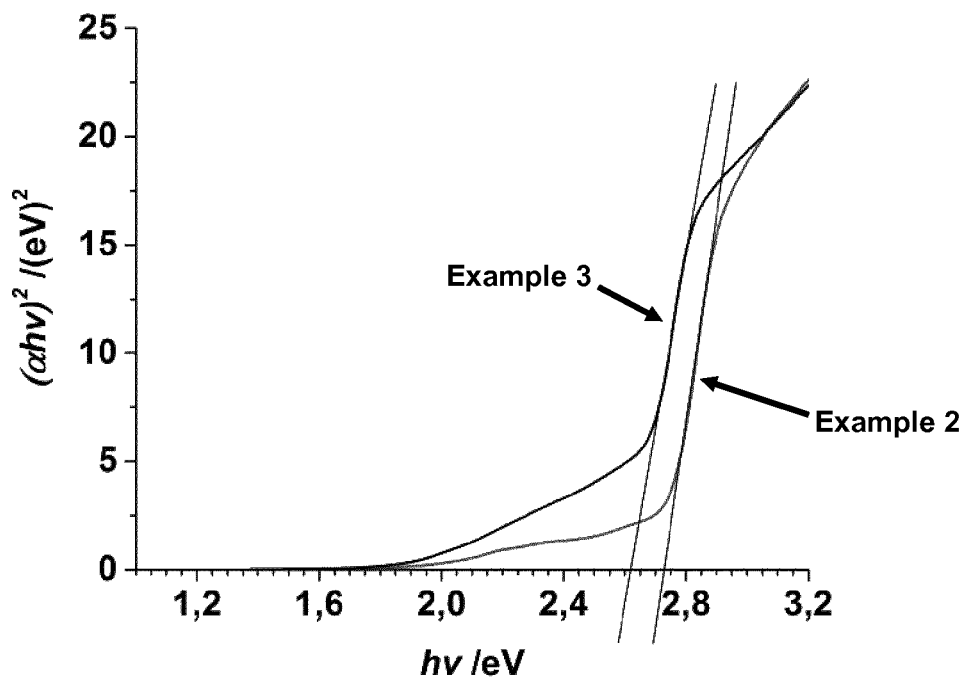
FIG. 5 shows the tauc plot for calculating the optical band gap for potassium poly(heptazine imides) prepared according to examples 2 and 3.

FIG. 5 shows the tauc plot for calculating the optical band gap for potassium poly(heptazine imides) prepared according to examples 2 and 3.

Figure 6:
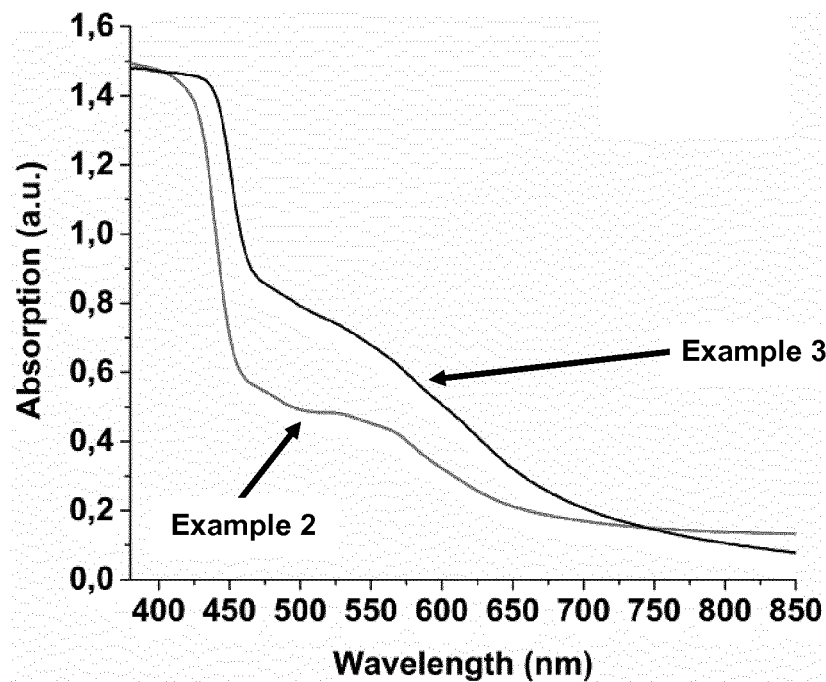
FIG. 6 shows the UV-VIS adsorption spectra for potassium poly(heptazine imides) prepared according to examples 2 and 3.

FIG. 6 shows the UV-VIS adsorption spectra for potassium poly(heptazine imides) prepared according to examples 2 and 3.

Figure 7:
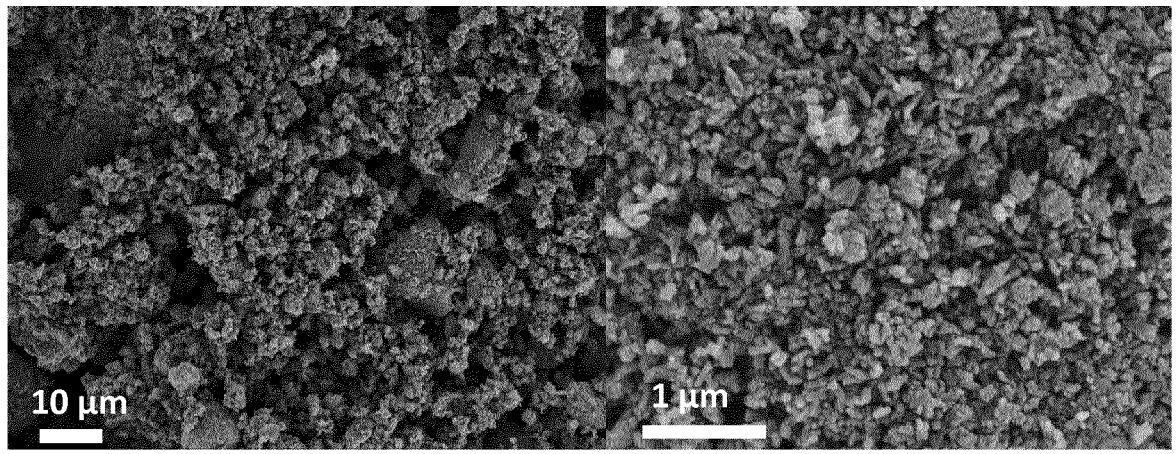
FIGS. 7a and 7b show TEM pictures for potassium poly(heptazine imides) prepared according to example 3.
FIGS. 7c and 7d show TEM pictures for potassium poly(heptazine imides) prepared according to example 2.
Figure 7:
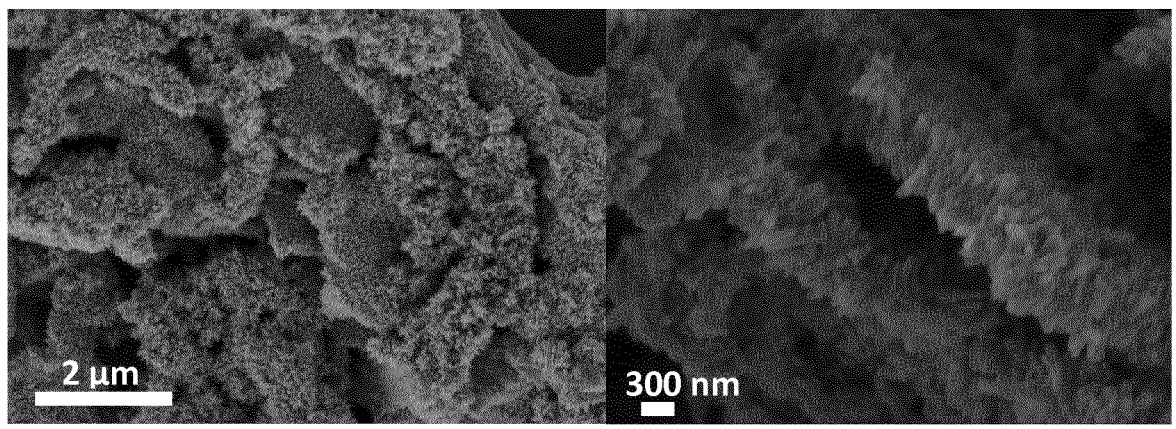

FIGS. 7a and 7b show TEM pictures for potassium poly(heptazine imides) prepared according to example 3.

FIGS. 7c and 7d show TEM pictures for potassium poly(heptazine imides) prepared according to example 2.

Examples 4 to 26: Reaction Type A—Thiolation of Benzylic C—H Bonds to Obtain diaryldisulfanes A General Procedure for the Preparation of (Substituted) dibenzyldisulfanes A screw-capped tube was charged with potassium poly (heptazine imide) obtained according to example 2 (10 mg), methylarene (0.3 mL), elemental sulfur (alpha-S$_8$, 0.96 g, 30 μmol) and acetonitrile (2.7 mL). The teflon coated stir bar was placed as well. The suspension was frozen in liquid nitrogen to solid state and evacuated till the residual pressure 0.1 mbar. The solid was warmed using the heating gun until the solid has molten. The procedure was repeated 3 times and the tube was refilled with argon. The suspension was vigorously stirred at +50° C. under blue LED (461 nm, 0.0517±3·10$^{-5}$ W·cm$^{-2}$) irradiation for 24 hours. The reaction mixture was allowed to cool to room temperature and the tube was opened. A distinct smell of H$_2$S was detected. Catalyst was separated by centrifugation (13000 min$^{-1}$) and washed with acetonitrile (3×1.5 mL). The washings were combined and acetonitrile evaporated under reduced pressure (+50° C., 80 mbar). The residue was washed with chloroform (3×2 mL) and undissolved particles were separated by centrifugation (13000 min$^{-1}$). Evaporation of chloroform under reduced pressure furnished corresponding diaryldisulfanes.

Example 4: Preparation of 1,2-dibenzyldisulfane from toluene

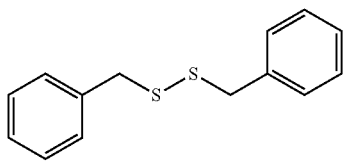 [SMILES: c1ccc(CSSCc2ccccc2)cc1]

Yield: 56%. $^1$H, $^{13}$C NMR, FTIR spectra were identical to the authentic sample. $^1$H NMR (400 MHz, CDCl$_3$): δ=3.60 (s, 4H, CH$_2$), 7.23-7.34 (m, 10H, CH). $^{13}$C NMR (400 MHz, CDCl$_3$): δ=43.2 (s, CH$_2$), 127.4 (s, CH), 128.5 (s, CH), 129.4 (s, CH), 137.3 (s, CH). MS (EI): 246.1 (M$^+$).

Example 5: Preparation of 1,2-bis(4-methoxybenzyl)disulfane from 4-methylanisole

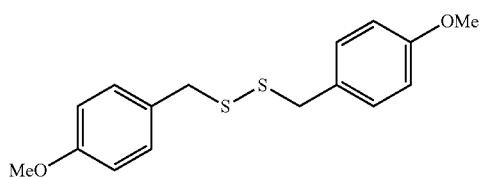 [SMILES: COc1ccc(CSSCc2ccc(OC)cc2)cc1]

Yield: 67%. $^1$H NMR (400 MHz, CDCl$_3$): δ=3.59 (s, 4H, CH$_2$), 3.80 (s, 6H, OCH$_3$), 6.85 (d, J$_{HH}$=8.8 Hz, CH, 4H), 7.17 (J$_{HH}$=8.8Hz, CH, 4H). $^{13}$C NMR (400 MHz, CDCl$_3$): δ=42.7 (s, CH$_2$), 55.3 (s, OCH$_3$), 113.9 (s, CH), 129.4 (s, C), 130.5 (s, CH). MS (EI): 306.1 (M$^+$).

Example 6: Preparation of 1,2-bis(2-methoxybenzyl)disulfane from 2-methylanisole

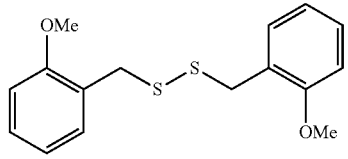 [SMILES: COc1ccccc1CSSCc1ccccc1OC]

Yield: 63%. $^1$H NMR (400 MHz, CDCl$_3$): δ=3.76 (s, 4H, CH$_2$), 3.86 (s, 6H, OCH$_3$), 6.85-6.92 (m, 4H, CH), 7.16 (dd, J$_{HH}$=7.2 Hz, J$_{HH}$=1.6 Hz), 7.25 (dt, J$_{HH}$=1.6 Hz, J$_{HH}$=8.0 Hz). $^{13}$C NMR (400 MHz, CDCl$_3$): δ=38.3 (s, CH$_2$), 55.5 (s, OCH$_3$), 110.6 (s, CH), 120.2 (s, CH), 125.8 (s, C), 128.8 (s, CH), 131.0 (s, CH). MS (EI): 306.1 (M$^+$).

Example 7: Preparation of 1,2-bis(1-phenylethyl)disulfane as a Mixture of diastereomers from ethylbenzene

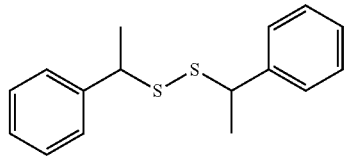 [SMILES: CC(SSC(C)c1ccccc1)c1ccccc1]

Yield: 47%. $^1$H NMR (400 MHz, CDCl$_3$): δ=3.52 (q, J$_{HH}$=7.0 Hz, 1H, CH), 3.60 (q, J$_{HH}$=7.0 Hz, 1H, CH), 1.54 (d, J$_{HH}$=7.0 Hz, 3H, CH), 1.55 (d, J$_{HH}$=7.0 Hz, 3H, CH), 7.21-7.34 (m, 10H, CH). $^{13}$C NMR (400 MHz, CDCl$_3$): δ=20.4 (s, CH$_3$), 20.5 (s, CH$_3$), 49.4 (s, CH), 49.5 (s, CH), 127.4 (s, CH), 127.5 (s, CH), 127.7 (s, CH), 127.8 (s, CH), 128.3 (s, CH), 128.4 (s, CH), 142.4 (s, C), 142.4 (s, C). MS (EI): 274.1 (M$^+$).

Example 8: Preparation of 1,2-bis(4-fluorobenzyl)disulfane from p-fluorotoluene

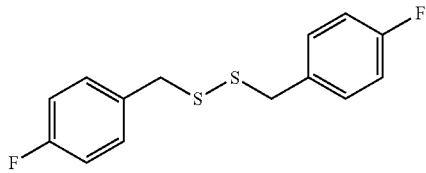 [SMILES: Fc1ccc(CSSCc2ccc(F)cc2)cc1]

Yield: 41%. $^1$H NMR (400 MHz, CDCl$_3$): δ=3.58 (s, 4H, CH$_2$), 7.01 (dd, J$_{HH}$=8.6 Hz, J$_{HH}$=8.6 Hz, 4H, CH), 7.20 (dd, J$_{HH}$=5.4 Hz, J$_{HH}$=8.6 Hz, 4H, CH). $^{13}$C NMR (400 MHz, CDCl$_3$): δ=42.4 (s, CH$_2$), 115.4 (d, J$_{CF}$=21.5 Hz, CH), 130.9 (d, J$_{CF}$=8.1 Hz, CH), 162.2 (d, J$_{CF}$=246.4 Hz, CF). MS (EI): 282.0 (M$^+$).

Example 9: Preparation of di-tert-butyl ((disulfanediylbis(methylene))bis(4,1-phenylene))dicarbamate from tert-butyl p-tolylcarbamate

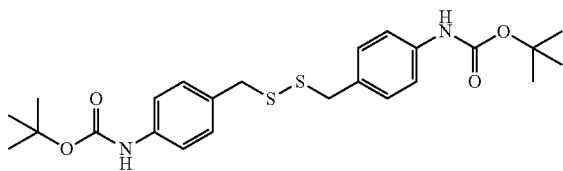 [SMILES: CC(C)(C)OC(=O)Nc1ccc(CSSCc2ccc(NC(=O)OC(C)(C)C)cc2)cc1]

Yield: 51%. $^1$H NMR (400 MHz, CDCl$_3$): δ=1.51 (s, 18H, CH$_3$), 3.58 (s, 4H, CH$_2$), 6.46 (br. s., 2H, NH), 7.15 (d, J$_{HH}$=8.0 Hz, CH, 4H), 7.31 (d, J$_{HH}$=8.0 Hz, 4H, CH). $^{13}$C NMR (400 MHz, CDCl$_3$): δ=28.3 (s, CH$_3$), 42.8 (s, CH$_2$), 118.4 (s, CH), 130.0 (s, CH), 131.8 (s, C), 137.6 (s, C), 152.6 (s, C).

Examples 10 to 20

Toluene was reacted following the general procedure given above but using different temperatures, different amounts of potassium poly(heptazine imide) obtained according to example 2 (K-PHI) and varying solvents (each 2.7 mL if not indicated otherwise).

The results are summarized in table 1.

TABLE 1

| Example | K-PHI, mg | Solvent | T, ° C. | Dibenzyldisulfane yield,$^a$ μmol |
|---|---|---|---|---|
| 10 | 5 | MeCN | 30 | 0.9293 |
| 11 | 5 | PhCH$_3$ | 30 | 1.3588$^c$ |
| 12 | 5 | MeCN | 50 | 5.855 |
| 13$^b$ | 5 | MeCN | 50 | 4.45 |
| 14$^b$ | 10 | MeCN | 50 | 5.105 |
| 15$^b$ | 20 | MeCN | 50 | 3.940$^e$ |
| 16 | 5 | PhCH$_3$ | 50 | 1.486$^c$ |
| 17 | 5 | CH2Cl$_2$ | 50 | 0.2195 |
| 18 | 5 | MeCN | 80 | 2.213 |
| 19 | 5 | PhCH$_3$ | 80 | 2.652$^c$ |
| 20 | 5 | pyridine | 80 | 0.9164 |

$^a$determined by GC-MS using naphthalene as internal standard;
$^b$PhCH$_3$ 0.2 mL; S$_8$ 31 μmol;

Examples 21 to 26

Toluene was reacted following the general procedure given above but using different temperatures, alternative photocatalysts for comparative purposes and varying excitation wavelengths.

The results are summarized in table 2.

TABLE 2

| Example | Photocatalyst | T, ° C. | Light | Bn$_2$S$_2$ yield,$^a$ % |
|---|---|---|---|---|
| 21 | K-PHI | 30 | 461 nm | 9.3 |
| 22 | K-PHI | 50 | 461 nm | 74.5 |
| 23 | K-PHI | 80 | 461 nm | 22.1 |
| 24 | K-PHI | 50 | 372 nm | 50.2 |
| 25 (for comparison) | TiO$_2$ | 50 | 372 nm | 0.0 |
| 26 (for comparison) | mpg-CN | 50 | 461 nm | 2.4 |

Examples 27 to 41: Reaction Type B—Thiolation of Amines to Obtain Thioamides

General Method for the Preparation of Thioamides from a Single Amine

A glass tube with rubber-lined cap was evacuated and filled with argon three times. To this tube the respective amine (0.5 mmol), sulphur (1.5 mmol), potassium poly (heptazine imide) obtained according to example 2 (10 mg) and corresponding solvent (2 mL) were added. The resulting mixture was stirred at temperature listed at Scheme 4 under irradiation of Blue LED (461 nm, 79 mW·cm$^{-2}$) for time listed at Scheme 4. Then reaction mixture was cooled to room temperature and centrifuged, clear solution was separated and solid residue was washed with dioxane (2 mL) and centrifuged again. Organic solutions were combined and evaporated to dryness. Thioamides prepared according to examples 28, 29, 30, 32, 33, 35 were obtained by recrystallization of crude residue after evaporation in mixture ethyl acetate/hexane (1:4) and thioamides 27, 31, 34, 36 and 37 were purified by flash silica gel column chromatography using mixture of diethyl ether/dichloromethane (1:2) as an eluent.

Example 27: Preparation of N-Benzylbenzothioamide from benzylamine

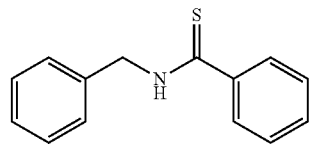 [SMILES: S=C(NCc1ccccc1)c1ccccc1]

Yellowish solid (yield 90%), m.p. 84-85° C.

$^1$H NMR (400 MHz, DMSO-d$_6$) δ 10.75 (s, 1H), 7.75 (d, J=7.0 Hz, 2H), 7.46 (m, 1H), 7.40 (m, 2H), 7.36-7.28 (m, 4H), 7.24 (m, 1H), 4.95 (d, J=5.9 Hz, 2H).

$^{13}$C NMR (101 MHz, CDCl$_3$) δ 199.1, 141.6, 136.2, 131.2, 129.0, 128.5, 128.4, 128.2, 126.7, 51.0.

HRMS m/z (EI, [M+H]$^+$): C$_{14}$H$_{14}$NS$^+$calcd 228.0847, found 228.0852.

Example 28: Preparation of 3-Methyl-N-(3-methylbenzyl)benzothioamide from 3-methylbenzylamine

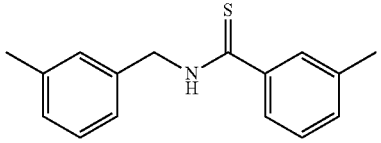

Yellowish solid (yield 92%), m.p. 84-86° C.

$^1$H NMR (400 MHz, CDCl$_3$) δ 7.66 (br s, 1H), 7.59 (s, 1H), 7.50 (m, 1H), 7.30-7.12 (m, 6H), 4.93 (d, J=5.0 Hz, 2H), 2.36 (br s, 6H).

$^{13}$C NMR (101 MHz, CDCl$_3$) δ 199.2, 141.6, 138.8, 138.4, 136.1, 131.9, 129.2, 128.9, 128.4, 127.7, 125.4, 123.4, 51.1, 21.4, 21.4.

HRMS m/z (EI, [M+H]$^+$): C$_{16}$H$_{18}$NS$^+$ calcd 256.1160, found 256.1168.

Example 29: Preparation of 4-methyl-N-(4-methylbenzyl)benzothioamide from 4-methylbenzylamine

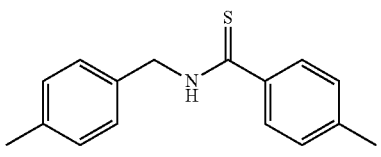

Yellowish solid (yield 90%), m.p. 75-76° C.

$^1$H NMR (400 MHz, DMSO-d$_6$) δ 10.60 (s, 1H), 7.67 (d, J=8.2 Hz, 2H), 7.20 (m, 4H), 7.11 (d, J=7.9 Hz, 2H), 4.89 (d, J=5.9 Hz, 2H), 2.30 (s, 3H), 2.24 (s, 3H).

$^{13}$C NMR (101 MHz, DMSO-d$_6$) δ 197.6, 141.2, 138.7, 136.6, 134.9, 129.3, 128.9, 128.0, 127.8, 49.1, 21.3, 21.1.

HRMS m/z (EI, [M+H]$^+$): C$_{16}$H$_{18}$NS$^+$ calcd 256.1160, found 256.1154.

Example 30: Preparation of 4-methoxy-N-(4-methoxybenzyl)benzothioamide from 4-methoxybenzylamine

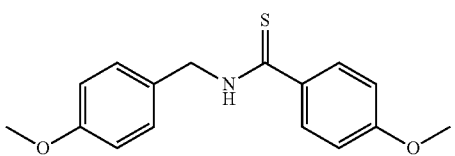

Yellowish solid (yield 91%), m.p. 92-94° C. (Lit.$^{22}$ m.p. 91-94° C.)

$^1$H NMR (400 MHz, DMSO-d$_6$) δ 10.49 (s, 1H), 7.79 (d, J=8.9 Hz, 2H), 7.27 (d, J=8.6 Hz, 2H), 6.93 (d, J=8.9 Hz, 2H), 6.87 (d, J=8.7 Hz, 2H), 4.86 (d, J=5.8 Hz, 2H), 3.77 (s, 3H), 3.69 (s, 3H).

$^{13}$C NMR (101 MHz, DMSO-d$_6$) δ 196.5, 161.9, 158.8, 133.5, 130.0, 129.7, 129.5, 114.1, 113.6, 55.9, 55.5, 48.9.

HRMS m/z (EI, [M+H]$^+$): C$_{16}$H$_{18}$NO$_2$S$^+$ calcd 288.1058, found 288.1051.

Example 31: Preparation of 4-amino-N-(4-aminobenzyl)benzothioamide from 4-aminomethyl-aniline

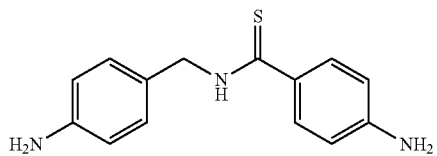 [SMILES: Nc1ccc(CNC(=S)c2ccc(N)cc2)cc1]

Yellowish solid (yield 82%), m.p. 79-81° C.

$^1$H NMR (400 MHz, CDCl$_3$) δ 7.65 (d, J=8.5 Hz, 2H), 7.39 (br s, 1H), 7.17 (d, J=8.2 Hz, 2H), 6.67 (d, J=8.2 Hz, 2H), 6.58 (d, J=8.5 Hz, 2H), 4.82 (d, J=4.7 Hz, 2H), 3.94 (br s, 2H), 3.71 (br s, 2H).

$^{13}$C NMR (101 MHz, CDCl$_3$) δ 197.1, 149.6, 146.4, 129.8, 128.6, 128.2, 126.2, 115.3, 113.9, 50.9.

HRMS m/z (EI, [M+Na]$^+$): C$_{14}$H$_{15}$N$_3$SNa$^+$ calcd 280.0884, found 280.0878.

Example 32: Preparation of N-(pyridin-2-ylmethyl)pyridine-2-carbothioamide from 2-aminomethyl-pyridine

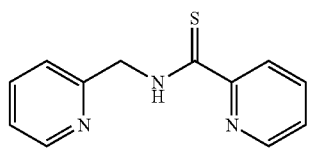 [SMILES: S=C(NCc1ccccn1)c1ccccn1]

Yellowish solid (yield 88%), m.p. 91-92° C.

$^1$H NMR (400 MHz, DMSO-d$_6$) δ 11.38 (s, 1H), 8.64 (d, J=5.5 Hz, 1H), 8.54 (d, J=5.4 Hz, 1H), 8.50 (d, J=7.9 Hz, 1H), 7.99 (t, J=7.8 Hz, 1H), 7.75 (t, J=7.7 Hz, 1H), 7.62 (dd, J=7.4, 4.8 Hz, 1H), 7.32 (d, J=7.8 Hz, 1H), 7.30-7.25 (m, 1H), 5.05 (d, J=5.6 Hz, 2H).

$^{13}$C NMR (101 MHz, CDCl$_3$) δ 190.9, 155.0, 151.3, 149.4, 147.3, 137.1, 136.8, 126.0, 124.8, 122.6, 122.2, 50.5.

HRMS m/z (EI, [M+H]$^+$): C$_{12}$H$_{12}$N$_3$S$^+$ calcd 230.0752, found 230.0754.

Example 33: Preparation of N-(pyridin-3-ylmethyl)pyridine-3-carbothioamide from 3-aminomethyl-pyridine

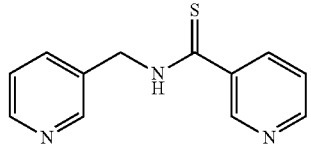 [SMILES: S=C(NCc1cccnc1)c1cccnc1]

Yellowish solid (yield 89%), m.p. 88-90° C.

$^1$H NMR (400 MHz, DMSO-d$_6$) δ 11.00 (s, 1H), 8.93-8.81 (m, 1H), 8.66-8.52 (m, 2H), 8.46 (dd, J=4.8, 1.6 Hz,

1H), 8.13-8.04 (m, 1H), 7.77 (dt, J=7.8, 1.8 Hz, 1H), 7.44 (dd, J=8.4, 4.4 Hz, 1H), 7.35 (dd, J=7.5, 5.1 Hz, 1H), 4.94 (d, J=5.6 Hz, 2H).

$^{13}$C NMR (101 MHz, DMSO-$d_6$) δ 195.8, 151.8, 149.7, 148.9, 148.0, 136.9, 136.0, 135.4, 133.1, 124.0, 123.5, 47.3.

HRMS m/z (EI, [M+H]$^+$): $C_{12}H_{12}N_3S^+$ calcd 230.0752, found 230.0760.

Example 34: Preparation of N-(pyridin-4-ylmethyl)pyridine-4-carbothioamide from 4-aminomethyl-pyridine

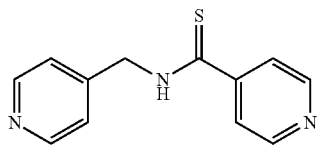 [SMILES: S=C(NCc1ccncc1)c1ccncc1]

Yellowish solid (yield 68%), m.p. 109-110° C.

$^1$H NMR (400 MHz, CDCl$_3$) δ 8.69 (d, J=6.1 Hz, 2H), 8.61 (d, J=6.0 Hz, 2H), 7.96 (s, 1H), 7.58 (d, J=6.1 Hz, 2H), 7.28 (d, J=5.9 Hz, 2H), 5.06 (d, J=5.7 Hz, 2H).

$^{13}$C NMR (101 MHz, CDCl$_3$) δ 197.63, 150.34, 150.22, 147.77, 144.84, 122.65, 120.52, 49.02.

MS (EI): 229 (M$^+$). HRMS m/z (EI, [M-HS]$^+$): $C_{12}H_{10}N_3^+$ calcd 196.0874, found 196.0862.

Example 35: Preparation of N-(furan-2-ylmethyl)furan-2-carbothioamide from furan-2-ylmethylamine.

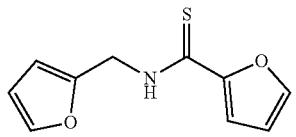 [SMILES: S=C(NCc1ccco1)c1ccco1]

Brown solid (yield 85%), m.p. 103-104° C.

$^1$H NMR (400 MHz, DMSO-$d_6$) δ 10.48 (s, 1H), 7.87 (m, 1H), 7.56 (m, 1H), 7.22 (d, J=3.5 Hz, 1H), 6.60 (m, J=3.5, 1.7 Hz, 1H), 6.39-6.36 (m, 1H), 6.30 (d, J=3.1 Hz, 1H), 4.87 (d, J=5.7 Hz, 2H).

$^{13}$C NMR (101 MHz, DMSO-$d_6$) δ 182.1, 152.3, 150.7, 145.9, 142.7, 117.0, 113.3, 111.0, 108.5, 41.2.

HRMS m/z (EI, [M+H]$^+$): $C_{10}H_{10}NO_2S^+$ calcd 208.0432, found 208.0439.

Example 36: Preparation of N-butylbutanethioamide from n-butylamine

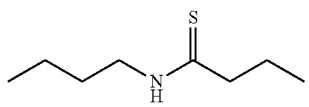

Orange oil (yield 72%)

$^1$H NMR (400 MHz, CDCl$_3$) δ 7.10 (s, 1H), 3.69-3.61 (m, 2H), 2.63-2.55 (m, 2H), 1.79 (m, 2H), 1.62 (m, 2H), 1.38 (m, 7.4 Hz, 2H), 0.94 (m, 6H).

$^{13}$C NMR (101 MHz, CDCl$_3$) δ 205.3, 49.3, 45.8, 30.1, 22.7, 20.2, 13.7, 13.3.

HRMS m/z (EI, [M+H]$^+$): $C_8H_{18}NS^+$ calcd 160.1160, found 160.1172.

Example 37: Preparation of N-hexylhexanethioamide from n-hexylamine

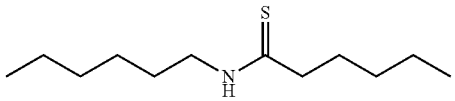

Brown oil (yield 78%)

$^1$H NMR (400 MHz, CDCl$_3$) δ 7.12 (s, 1H), 3.70-3.57 (m, 2H), 2.67-2.56 (m, 2H), 1.75 (m, 2H), 1.63 (m, 2H), 1.30 (m, 10H), 0.87 (t, J=6.8 Hz, 6H).

$^{13}$C NMR (101 MHz, CDCl$_3$) δ 205.5, 47.4, 46.1, 31.4, 31.1, 29.1, 28.0, 26.6, 22.5, 22.4, 14.0, 13.9.

MS (EI): 215 (M$^+$). HRMS m/z (EI, [M-HS]$^+$): $C_{12}H_{24}N^+$ calcd 182.1908, found 182.1890.

General Method for the Preparation of Thioamides from Two Different Amines

A glass tube with rubber-lined cap was evacuated and filled with argon three times. To this tube benzylamine (0.5 mmol), a secondary amine (1.5 mmol), sulfur (3 mmol), potassium poly(heptazine imide) obtained according to example 2 (10 mg) and dioxane (4 mL) were added. The resulting mixture was stirred at 70° C. under irradiation with Blue LED (461 nm, 79 mW·cm$^{-2}$) for 20 hours. Then the reaction mixture was cooled to room temperature and centrifuged, clear solution was separated and solid residue was washed with dioxane (2×2 mL) and centrifuged again. Organic solutions were combined, evaporated to dryness, dissolved in dichlormethane (3 mL) and washed with distilled water (2×2 mL). The organic layer was dried over Na$_2$SO$_4$ and evaporated to dryness. Thioamides were obtained after flash silica gel column chromatography by using mixtures of ethyl acetate/hexane (1:4) for thioamides according to examples 38 and 39 and diethyl ether/dichlormethan (1:2) for the thioamide according to example 40 as eluents.

Example 38: Preparation of 1-thiobenzoyl pyrrolidine from benzylamine and pyrrolidine

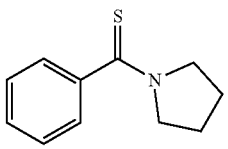 [SMILES: S=C(c1ccccc1)N1CCCC1]

Pale yellow solid (yield 83%), m.p. 68-71° C.

$^1$H NMR (400 MHz, CDCl$_3$) δ 7.38-7.28 (m, 5H), 3.97 (t, J=7.1 Hz, 2H), 3.45 (t, J=6.7 Hz, 2H), 2.07 (p, J=6.8 Hz, 2H), 1.95 (p, J=6.8 Hz, 2H).

$^{13}$C NMR (101 MHz, CDCl$_3$) δ 197.3, 144.0, 128.7, 128.3, 125.6, 53.8, 53.4, 26.5, 24.6.

HRMS m/z (EI, [M+H]$^+$): $C_{11}H_{14}NS^+$ calcd 192.0847, found 192.0859.

Example 39: Preparation of 1-Thiobenzoyl piperidine from benzylamine and piperidine

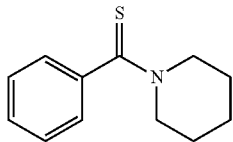 [SMILES: S=C(c1ccccc1)N1CCCCC1]

Pale yellow solid (yield 72%), mp. 63-64° C.
$^1$H NMR (400 MHz, CDCl$_3$) δ 7.35-7.29 (m, 3H), 7.26-7.23 (m, 2H), 4.43-4.26 (m, 2H), 3.54-3.45 (m, 2H), 1.81 (m, 2H), 1.73 (m, 2H), 1.55 (m, 2H).
$^{13}$C NMR (101 MHz, CDCl$_3$) δ 199.6, 143.4, 128.4, 128.3, 125.4, 53.1, 50.6, 26.9, 25.5, 24.2.
HRMS m/z (EI, [M+H]$^+$): C$_{12}$H$_{16}$NS$^+$ calcd 206.1003, found 206.1015.

Example 40: Preparation of (3,4-dihydroisoquinoline-2(1H)-yl)(phenyl)methanethione from benzylamine and 3,4-dihydroisoquinoline-2(1H)

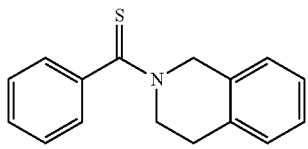 [SMILES: S=C(c1ccccc1)N1CCc2ccccc2C1]

Yellow solid (yield 76%), mp. 77-78° C.
$^1$H NMR (400 MHz, CDCl$_3$) (two rotamers) δ 7.40-7.12 (m, 8H), 6.87 (d, J=7.7 Hz, 1H), 5.38 (s, 1H), 4.67 (s, 1H), 4.49 (t, J=6.2 Hz, 1H), 3.81-3.71 (m, 1H), 3.12 (t, J=6.2 Hz, 1H), 2.89 (t, J=5.8 Hz, 1H).
$^{13}$C NMR (101 MHz, CDCl$_3$) δ 200.7, 200.1, 143.2, 134.9, 133.4, 132.3, 128.8, 128.7, 128.5, 128.5, 128.4, 128.3, 127.5, 127.0, 126.9, 126.9, 126.6, 126.0, 125.7, 53.9, 52.1, 49.9, 48.4, 29.8, 28.0.
HRMS m/z (EI, [M+H]$^+$): C$_{16}$H$_{16}$NS$^+$ calcd 254.1003, found 254.1009.

Example 41: Preparation of 3-(aminomethyl)-N-(3-(aminomethyl)benzyl)-benzo-thioamide and 4-(aminomethyl)-N-(4-((4-(aminomethyl)benzyl)-carbamothioyl)-benzyl)benzothioamide A glass tube with rubber-lined cap was evacuated and filled with argon three times. To this tube p-xylylenediamine or m-xylylenediamine (68.1 mg, 0.5 mmol), sulphur (48 mg, 1.5 mmol), potassium poly(heptazine imide) (10 mg) and 4 ml of N,N-dimethylformamide (DMF) were added. Resulting mixture was stirred at 70° C. under irradiation of Blue LED (461 nm, 79 mW/cm$^2$) for 20 hours (or alternatively at room temperature for 90 hours). After that reaction mixture was cooled to room temperature and centrifuged (13,000 min$^{-1}$, 3 min). A clear solution was separated and solid residue was washed with 1 ml of DMF and centrifuged again (13,000 min$^{-1}$, 3 min). DMF solutions were combined and added dropwise into 20 ml of diethyl ether. Obtained yellowish precipitate was separated by filtration and washed twice with 20 ml of diethyl ether, then dried in vacuum at 50° C.

Examples 42 to 53: Reaction type C)—Oxidation of Alcohols to Aldehydes or Ketones

General Method for the Preparation of benzaldehyde

A mixture of benzyl alcohol (0.5 mmol), varying amounts of potassium poly(heptazine imide) obtained according to example 2 (K-PHI) or other photocatalysts, elemental sulfur (alpha-S$_8$ abbreviated as S$_8$, 48 mg) as electron acceptor if not mentioned otherwise and ZnO where indicated in MeCN (6 mL) was stirred at +50° C. under N$_2$ and irradiation with a blue light (40 W, 465 nm) for 24 h. The catalyst was separated by centrifugation (12000 min$^{-1}$, 1 min) and washed with MeCN (2×1 mL). Solvent evaporation afforded the benzaldehyde [a].

The Catalyst Used in Example 45 was Reused in Experiments 46 to 48 to Assess Recyclability and Stability The results of catalytic tests are summarized in Table 3.

TABLE 3

| Example | Catalyst | Electron acceptor | T, ° C. | Conversion[b], % | Selectivity[c], % |
|---|---|---|---|---|---|
| 42 | K-PHI (10 mol.-%)[d] | S$_8$ | 20 | 81.3 | 95.5 |
| 43 | K-PHI (10 mol. %) | S$_8$ | 50 | 84.4 | 99.5 |
| 44 | K-PHI (20 mol. %) | S$_8$ | 50 | 90.7 | 99.8 |
| 45 | K-PHI (10 mol. %) + ZnO (1 mmol) | S$_8$ | 50 | 99.2 | 98.4 |
| 46 | K-PHI (10 mol. %) + ZnO (1 mmol)[e] | S$_8$ | 50 | 99.6 | 97.5 |
| 47 | K-PHI (10 mol. %) + ZnO (1 mmol)[f] | S$_8$ | 50 | 99.5 | 98.6 |
| 48 | K-PHI (10 mol. %) + ZnO (1 mmol)[g] | S$_8$ | 50 | 99.5 | 99.3 |
| 49 | ZnO (1 mmol) | S$_8$ | 50 | 1.6 | 100 |
| 50 | none | S$_8$ | 50 | 0.2 | 100 |
| 51 | K-PHI (10 mol. %) | O$_2$[h] | 50 | 29.0 | 70.5 |
| 52 | K-PHI [i] (10 mol. %) + ZnO (1 mmol) | S$_8$ | 50 | 50.8 | 99.5 |
| 53 | mpg-CN (10 mol. %) + ZnO(1 mmol) | S$_8$ | 50 | 37.9 | 99.6 |

[a] Benzyl alcohol: 0.5 mmol; MeCN 6 mL; S$_8$: 1.5 mmol.
[b]Conversion of benzyl alcohol according to GC-MS data using ethylbenzene as an internal standard.
[c]Selectivity with respect to benzaldehyde formation.
[d]the molar weight of K-PHIK taken for calculation is 438 g · mol$^{-1}$
[e]second run.
[f]third run.
[g]fourth run.
[h]O$_2$ pressure 1 bar.
[i] potassium poly(heptazine imide) obtained according to example 3

Examples 54 to 56: Reaction Types C) and D)—Oxidation of Alcohols to Aldehydes or Ketones and Conversion of dihydropyridines to pyridines Example 54: Preparation of diethyl 2,4,6-trimethyl-1,4-dihydropyridine-3,5-dicarboxylate Via Intermediary Oxidation of ethanol to acetaldehyde A mixture of ethyl 3-oxobutanoate (0.23 g, 1.8 mmol), $NH_4HCO_3$ (70 mg, 0.9 mmol), potassium poly(heptazine imide) obtained according to example 2 (100 mg), $S_8$ (240 mg, 7.5 mmol) and ZnO (405 mg, 5 mmol) in EtOH (40 mL) was stirred under $N_2$ at +50° C. under blue LED (40 W, 465 nm) irradiation for 24 h. Reaction progress was monitored by GC-MS. Catalyst was separated by centrifugation (12000 $min^{-1}$, 2 min) and washed with ethanol (3×2mL). Ethanol washings were combined, solvent was evaporated under reduced pressure and residue was dried in vacuum. MeCN (40 mL) was added to the residue followed by the addition of PHIK-BM (100 mg), $S_8$ (240 mg) and ZnO (405 mg). The suspension was stirred under blue LED (40 W, 465 nm) irradiation under $N_2$ was continued for another 18 h. Catalyst was separated by centrifugation (12000 $min^{-1}$, 2 min) and washed with MeCN (3×2 mL). Washings were combined and concentrated in vacuum affording orange oil. Oil was washed with hexane (3×5 mL), extracts were combined and concentrated in vacuum affording 200 mg of yellow oil. Yield: 85%. $^1$H NMR (400 MHz, $CDCl_3$, δ): 4.41 (q, J=5.3 Hz, 4H, $CH_2$), 2.52 (s, 6H, $CH_3$), 2.27 (s, 3H, $CH_3$), 1.39 (t, J=5.3 Hz, 6H, $CH_3$).

Example 55: Preparation of diethyl 2,4,6-trimethylpyridine-3,5-dicarboxylate Via Intermediary Oxidations of Ethanol to Acetaldehyde and (!) diethyl 2,4,6-trimethyl-1,4-dihydropyridine-3,5-dicarboxylate A mixture of ethyl 3-oxobutanoate (0.23 g, 1.8 mmol), $NH_4HCO_3$ (70 mg, 0.9 mmol), potassium poly(heptazine imide) obtained according to example 2 (100 mg), $S_8$ (240 mg, 7.5 mmol) and ZnO (405 mg, 5 mmol) in EtOH (40 mL) was stirred under $N_2$ at +50° C. under blue LED (40 W, 465 nm) irradiation for 24 h. Reaction progress was monitored by GC-MS. Catalyst was separated by centrifugation (12000 $min^{-1}$, 2 min) and washed with ethanol (3×2 mL). Ethanol washings were combined, solvent was evaporated under reduced pressure and residue was dried in vacuum. MeCN (40 mL) was added to the residue followed by the addition of PHIK-BM (100 mg), $S_8$ (240 mg) and ZnO (405 mg). The suspension was stirred under blue LED (40 W, 465 nm) irradiation under $N_2$ was continued for another 18 h. Catalyst was separated by centrifugation (12000 $min^{-1}$, 2 min) and washed with MeCN (3×2 mL). Washings were combined and concentrated in vacuum affording orange oil. Oil was washed with hexane (3×5 mL), extracts were combined and concentrated in vacuum affording 200 mg of yellow oil. Yield: 85%. $^1$H NMR (400 MHz, $CDCl_3$, δ): 4.41 (q, J=5.3 Hz, 4H, $CH_2$), 2.52 (s, 6H, $CH_3$), 2.27 (s, 3H, $CH_3$), 1.39 (t, J=5.3 Hz, 6H, $CH_3$).

Example 56: Preparation of diethyl 2,6-dimethylpyridine-3,5-dicarboxylate Via Intermediary Oxidation of diethyl 2,6-dimethyl-1,4-dihydropyridine-3,5-dicarboxylate A mixture of diethyl 2,6-dimethyl-1,4-dihydropyridine-3,5-dicarboxylate (62.4 mg, 0.25 mmol), potassium poly(heptazine imide) obtained according to example 2 (20 mg), elemental sulfur (48 mg, 1.5 mmol), ZnO (81 mg, 1 mmol) in MeCN (6 mL) was stirred at +50° C. under $N_2$ and blue LED (40 W, 465 nm) irradiation for 24 h. Catalyst was separated by centrifugation (12000 $min^{-1}$, 1 min) and washed with MeCN (3×2 mL). Acetonitrile washings were combined and concentrated in vacuum affording white solid. Yield: 59 mg, 95%. $^1$H NMR (400 MHz, $CDCl_3$, δ): 8.68 (s, 1H, CH), 4.40 (q, J=5.4 Hz, 4H, $CH_2$), 2.85 (s, 6H, $CH_3$), 1.42 (t, J=5.4 Hz, 6H, $CH_3$).

Example 57: Reaction Type E)—Oxidative Conversion of N-carboxylated hydrazones to oxadiazoles Preparation of 2,5-diphenyl-1,3,4-oxadiazole A glass tube with rubber-lined cap was evacuated and filled with argon three times. To this tube (E)-N'-benzylidenebenzohydrazide (60 µmol), elemental sulphur (alpha-$S_8$, 6 mg, 0.18 mmol), potassium poly(heptazine imide) prepared according to example 2 (5 mg) and acetonitrile (2 mL) were added. The resulting mixture was stirred at 80° C. under irradiation of Blue LED (461 nm, 79 mW·$cm^{-2}$) for 20 hours. Then reaction mixture was cooled to room temperature and centrifuged (1 min at 2500 rpm), clear solution was separated and solid residue was washed with methanol (2 mL) and centrifuged again. Organic solutions were combined and evaporated to dryness. Residue after evaporation was purified by flash silica gel column chromatography using ethyl acetate/hexane (1:4) as an eluent.

Yield 76%. $^1$H NMR (400 MHz, Chloroform-d) δ 8.14 (dd, J=7.5, 2.2 Hz, 1H), 7.57-7.48 (m, 2H). $^{13}$C NMR (101 MHz, $CDCl_3$) δ 164.56, 131.71, 129.06, 126.92, 123.91.

The invention claimed is:
1. A photocatalytic system comprising
  at least one poly(heptazine imide) and
  at least one sulfur source that serves as an electron acceptor or reagent.
2. The photocatalytic system according to claim 1, wherein poly(heptazine imides) are compounds comprising repeating structural units of formula (I)

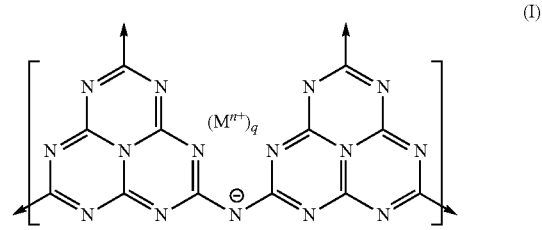

wherein
  the arrows each denote a bond to an imide group (—NH—) through which two structural units of formula (I) are linked together or a bond to an end group.
  $M^{n+}$ denotes an n-valent cation with n being 1, 2 or 3
  q is 1/n.
3. The photocatalytic system according to claim 2, wherein the poly(heptazine imides) are compounds comprising repeating structural units of formula (I) wherein $M^{n+}$ represents, $H^+$, $Li^+$, $Na^+$, $K^+$, $Rb^+$, $Cs^+$, $Ag^+$, $NH_4^+$, $Zn(OH)^+$, $Mg^{2+}$, $Ca^{2+}$, $Zn^{2+}$, $Co^{2+}$ or $Ni^{2+}$ or mixtures thereof.

4. The photocatalytic system according to claim 1, wherein the poly(heptazine imide) is potassium poly(heptazine imide) prepared by a process comprising at least the steps of
   a) providing a mixture comprising lithium chloride, potassium chloride and 5-aminotetrazole
   b) heating the mixture provided in step a) to a temperature of 450° C. to 700° C.

5. The photocatalytic system according to claim 4, wherein in the process to prepare potassium poly(heptazine imide) the weight ratio of 5-aminotetrazole to the sum of lithium chloride and potassium chloride employed is 1.0 or less.

6. The photocatalytic system according to claim 4, wherein in the process to prepare potassium poly(heptazine imide) lithium chloride, potassium chloride and 5-aminotetrazole are used in a particle size of 5 to 150 micrometers.

7. The photocatalytic system according to claim 1, wherein the poly(heptazine imide) carbon content is between 33.0 and 40.0, the nitrogen content is between 56.0 and 63.0 wt-%, and the hydrogen content between 0.2 and 4.0 wt-%, whereby the aforementioned contents are selected to add up to 100.0% and are based on the sum of carbon, nitrogen and hydrogen present in the poly(heptazine imide).

8. The photocatalytic system according to claim 1, wherein the poly(heptazine imide) is potassium poly(heptazine imide) having a potassium content of 8.5 to 11.5 wt-% based on the sum of carbon, nitrogen and hydrogen present in the potassium poly(heptazine imide).

9. The photocatalytic system according to claim 1, wherein the poly(heptazine imides) exhibit an optical band gap of 1.70 to 2.90 eV.

10. The photocatalytic system of claim 1, wherein the at least one sulfur source is elemental sulfur or polysulfides.

11. A process for the photocatalytic oxidation or photocatalytic thiolation of organic compounds comprising oxidation or thiolation of an organic compound carried out in the presence of a photocatalytic system according to claim 1 by irradiation.

12. The process according to claim 11, wherein thiolations are selected from the group consisting of thiolation of benzylic C—H bonds to obtain diaryldisulfanes or poly(aryldisulfanes) and thiolation of amines to thioamides or wherein oxidations are selected from the group consisting of oxidation of alcohols to aldehydes or ketones, oxidative conversion of dihydropyridines to pyridines and oxidative conversion of N-carboxylated hydrazones to oxadiazoles.

13. The process according to claim 11, comprising the preparation of a compound of formula (IIc)

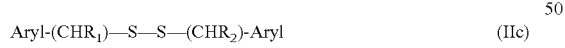

wherein
$R_1$ and $R_2$ are either different or identical and represent hydrogen or alkyl
and
Aryl represents aryl or heteroaryl
comprising irradiating a reaction mixture comprising
   a compound of formula (IIa)

wherein $R_1$ has the meaning set forth above
and if $R_2$ differs from $R_1$ additionally
   a compound of formula (IIb)

wherein $R_2$ has the meaning set forth above.

14. The process according to claim 11, comprising the preparation of a compound comprising a plurality of at least one of the structural units of formula (IIIc)

wherein
n+m is an integer of 2, 3, 4, 5 or 6
the n residues $R_3$ are either different or identical and represent hydrogen or alkyl and
Aryl represents aryl or heteroaryl which is substituted m-fold by residues ($CH_2R_3$) and n-fold by residues [($CHR_3$)—S]—
whereby the structural units of formula (IIIc) are bound together via a S—S bond formed by two [($CHR_3$)—S]—residues of two structural units of formula (IIIc)
comprising irradiating a reaction mixture comprising
   at least one compound of formula (IIIa)

wherein $R_3$ has the meaning set forth above.

15. The process according to claim 11, comprising the preparation of a compound of formula (IVb)

wherein
the two $R_4$ independently of each other represent hydrogen, alkyl, aryl, heterocyclyl, alkenyl or alkynyl
comprising irradiating a reaction mixture comprising
   at least one compound of formula (IVa)

wherein $R_4$ has the meaning set forth above.

16. The process according to claim 11 comprising the preparation of a compound of formula (Vc)

wherein
$R_5$ represents hydrogen, alkyl, aryl, heterocyclyl, alkenyl or alkynyl and
$R_6$ and $R_7$ independently of each other represent alkyl, aryl, heterocyclyl, alkenyl or alkynyl or
$R_6$ and $R_7$ together represent alkanediyl or alkenediyl
comprising irradiating a reaction mixture comprising
   at least one compound of formula (Va)

wherein $R_5$ has the meaning set forth above at least one compound of formula (Vb)

$$HNR_6R_7 \qquad (Vb)$$

wherein $R_6$ and $R_7$ have the meaning set forth above.

17. The process according to claim 11, wherein irradiation is effected with electromagnetic radiation having a wavelength of 200 to 700 nm.

\* \* \* \* \*